US007357287B2

(12) United States Patent
Shelton, IV et al.

(10) Patent No.: US 7,357,287 B2
(45) Date of Patent: Apr. 15, 2008

(54) SURGICAL STAPLING INSTRUMENT HAVING PRELOADED FIRING ASSISTANCE MECHANISM

(75) Inventors: Frederick E. Shelton, IV, Hillsboro, OH (US); Jeffrey S. Swayze, Hamilton, OH (US); Eugene L. Timperman, Cincinnati, OH (US); Leslie M. Fugikawa, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 82 days.

(21) Appl. No.: 11/238,291

(22) Filed: Sep. 29, 2005

(65) Prior Publication Data

US 2007/0068990 A1    Mar. 29, 2007

(51) Int. Cl.
*A61B 17/072* (2006.01)
*A61B 17/068* (2006.01)

(52) U.S. Cl. .............................. 227/178.1; 227/175.1; 227/19

(58) Field of Classification Search .. 227/175.1–182.1, 227/19; 606/139–145
See application file for complete search history.

(56) References Cited

U.S. PATENT DOCUMENTS

| | | | | |
|---|---|---|---|---|
| 2,442,416 A | * | 6/1948 | Kulicke, Jr. et al. ........ | 606/182 |
| 4,496,090 A | * | 1/1985 | Crevier et al. ................. | 227/19 |
| 4,674,504 A | * | 6/1987 | Klieman et al. ............. | 606/143 |
| 4,951,861 A | * | 8/1990 | Schulze et al. ........... | 227/178.1 |
| 5,286,255 A | * | 2/1994 | Weber ......................... | 604/22 |
| 5,464,144 A | * | 11/1995 | Guy et al. ................. | 227/176.1 |
| 5,465,895 A | * | 11/1995 | Knodel et al. ............ | 227/176.1 |
| 5,558,266 A | * | 9/1996 | Green et al. .............. | 227/178.1 |
| 5,632,433 A | * | 5/1997 | Grant et al. .............. | 227/179.1 |
| 5,645,209 A | * | 7/1997 | Green et al. .............. | 227/175.2 |
| 5,697,543 A | * | 12/1997 | Burdorff ................... | 227/176.1 |
| 5,738,474 A | * | 4/1998 | Blewett ....................... | 411/473 |
| 5,779,132 A | * | 7/1998 | Knodel et al. ............ | 227/176.1 |
| 5,816,471 A | * | 10/1998 | Plyley et al. ............. | 227/178.1 |
| 5,826,776 A | * | 10/1998 | Schulze et al. .......... | 227/176.1 |
| 5,878,938 A | * | 3/1999 | Bittner et al. ............. | 227/175.4 |
| 5,928,252 A | * | 7/1999 | Steadman et al. .......... | 606/148 |
| 6,644,532 B2 | * | 11/2003 | Green et al. .............. | 227/176.1 |
| 6,656,193 B2 | * | 12/2003 | Grant et al. ................ | 606/151 |
| 6,755,854 B2 | * | 6/2004 | Gillick et al. .............. | 623/1.11 |
| 6,786,382 B1 | * | 9/2004 | Hoffman ................... | 227/178.1 |
| 6,802,305 B1 | * | 10/2004 | Hatcher ....................... | 124/31 |
| 7,128,254 B2 | * | 10/2006 | Shelton et al. ........... | 227/181.1 |
| 2004/0199182 A1 | * | 10/2004 | Millimann et al. ......... | 606/139 |
| 2004/0232196 A1 | | 11/2004 | Shelton et al. | |
| 2005/0178813 A1 | | 8/2005 | Swayze et al. | |
| 2006/0229665 A1 | * | 10/2006 | Wales et al. ................ | 606/205 |
| 2006/0241655 A1 | * | 10/2006 | Viola ......................... | 606/142 |

* cited by examiner

*Primary Examiner*—Rinaldi I. Rada
*Assistant Examiner*—Lindsay Low
(74) *Attorney, Agent, or Firm*—Frost Brown Todd, LLC

(57) ABSTRACT

A surgical severing and stapling instrument clamps tissue in a staple applying assembly comprising a lower jaw of an elongate channel holding a staple cartridge and a pivotally opposed upper jaw (anvil). A firing handle drives a rack in a handle connected to a firing rod and bar that pass through an elongate shaft and into the staple applying assembly to sever and staple tissue. Upon release of the firing handle, a retraction spring assists in withdrawing the rack and other firing components. To advantageously assist in firing, a spring biased plunger is cocked prior to firing to impart assistance upon depression of the firing trigger. Alternatively, a torsion coil spring ratchet mechanism is preload to act through a gear into the rack to assist. As a further alternative, a retraction spring is preload and disengaged until the rack is fully fired.

22 Claims, 27 Drawing Sheets

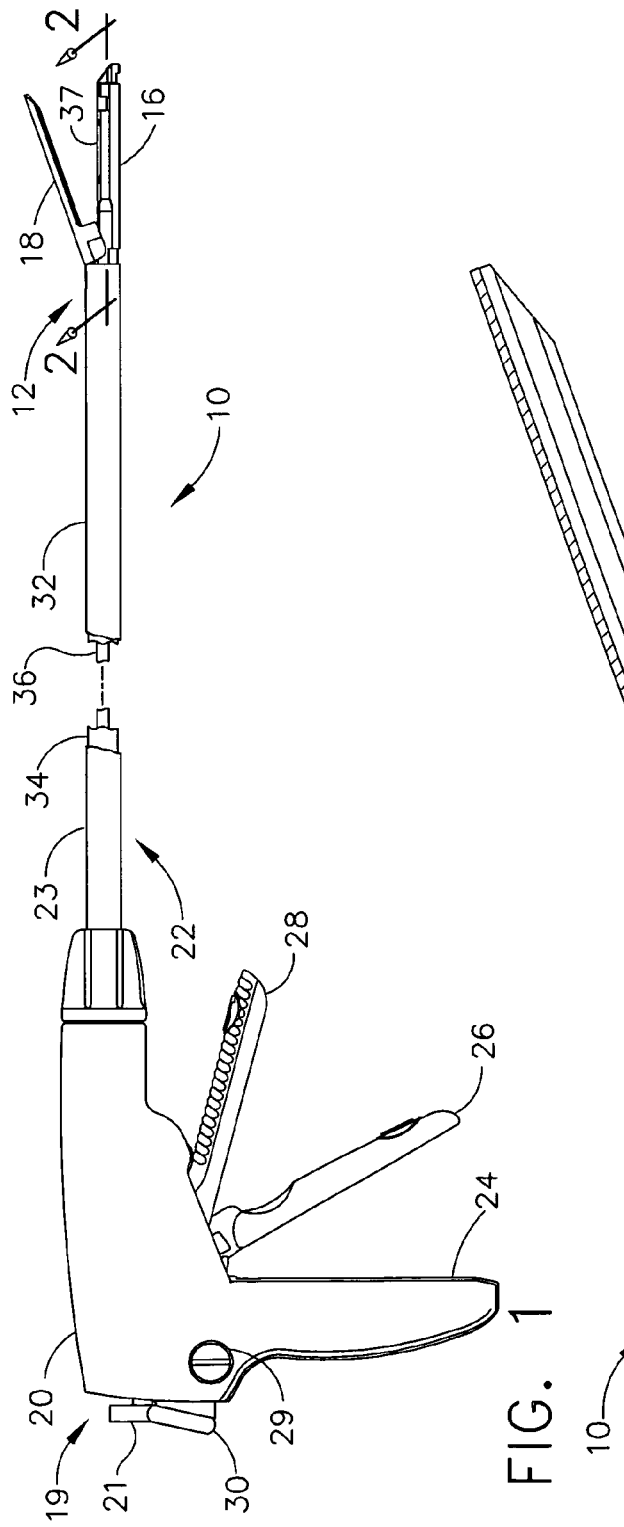
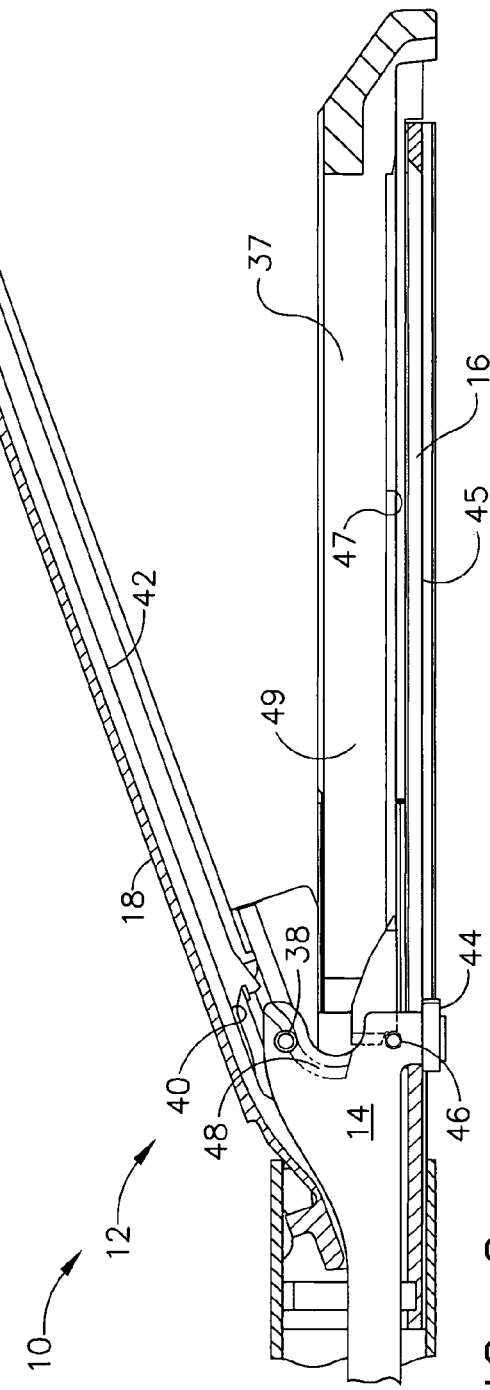
FIG. 1
FIG. 2

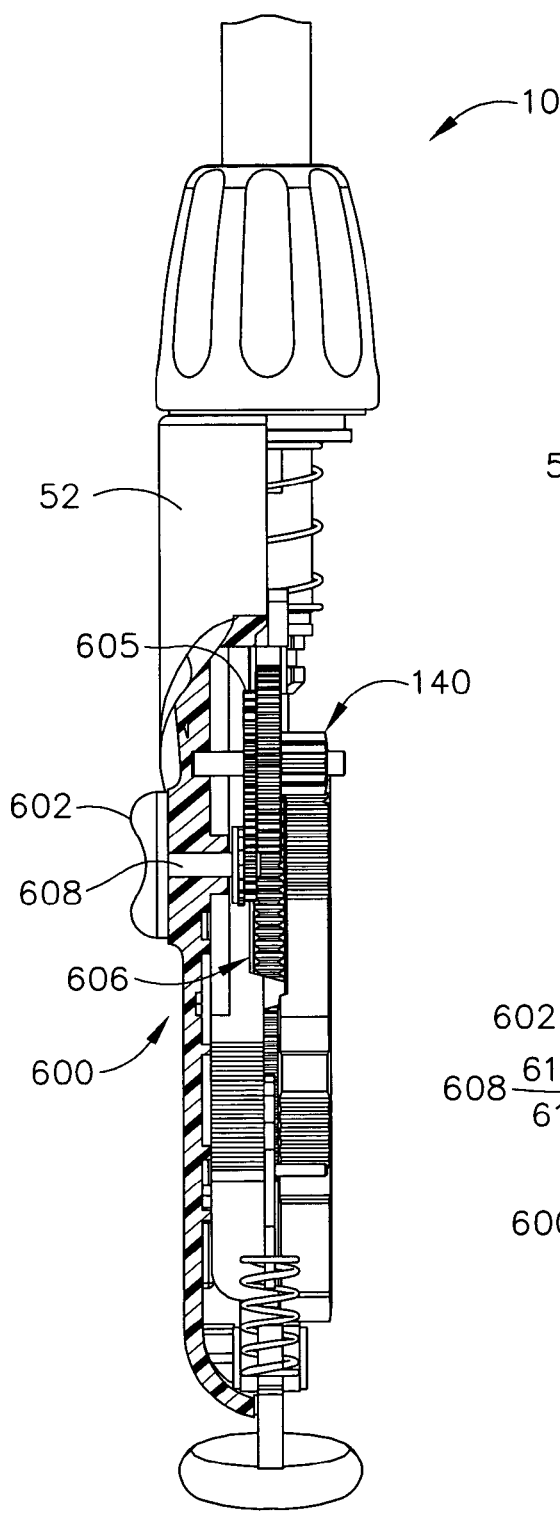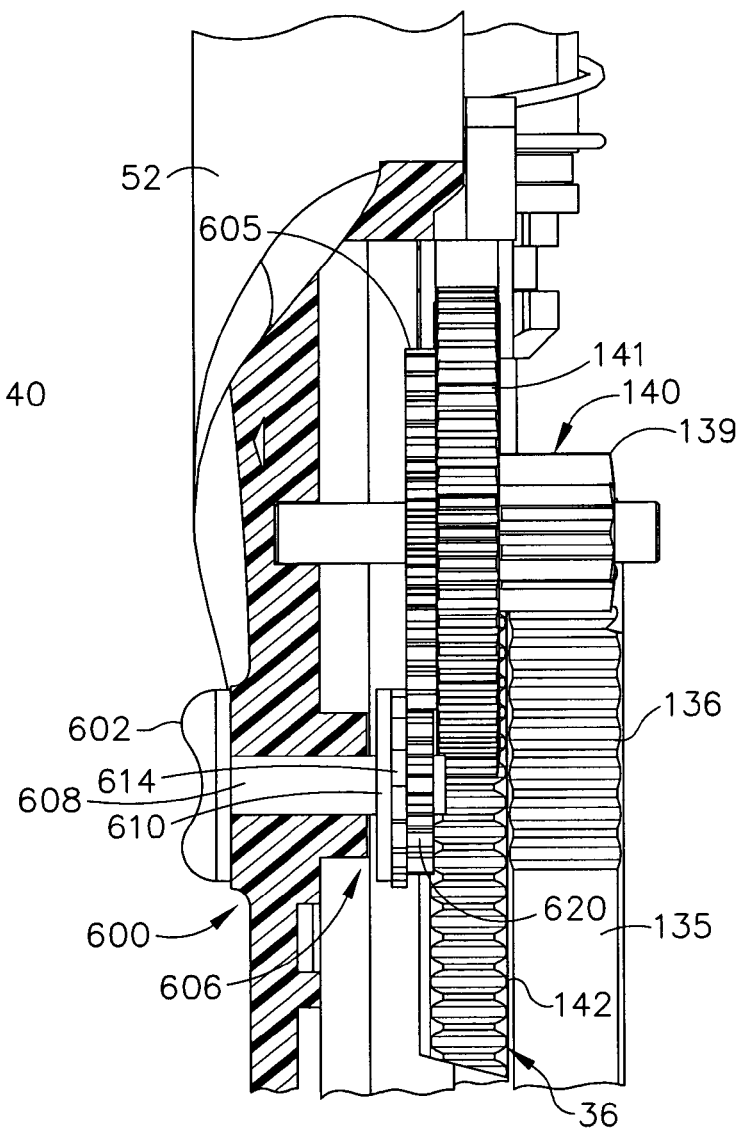
FIG. 35
FIG. 36

SURGICAL STAPLING INSTRUMENT HAVING PRELOADED FIRING ASSISTANCE MECHANISM

FIELD OF THE INVENTION

The present invention relates in general to surgical stapler instruments that are capable of applying lines of staples to tissue while cutting the tissue between those staple lines and, more particularly, to improvements relating to stapler instruments and improvements in processes for forming various components of such stapler instruments.

BACKGROUND OF THE INVENTION

Endoscopic and laparoscopic surgical instruments are often preferred over traditional open surgical devices since a smaller incision tends to reduce the post-operative recovery time and complications. The use of laparoscopic and endoscopic surgical procedures has been relatively popular and has provided additional incentive to develop the procedures further. In laparoscopic procedures, surgery is performed in the interior of the abdomen through a small incision. Similarly, in endoscopic procedures, surgery is performed in any hollow viscus of the body through narrow endoscopic tubes inserted through small entrance wounds in the skin.

Laparoscopic and endoscopic procedures generally require that the surgical region be insufflated. Accordingly, any instrumentation inserted into the body must be sealed to ensure that gases do not enter or exit the body through the incision. Moreover, laparoscopic and endoscopic procedures often require the surgeon to act on organs, tissues and/or vessels far removed from the incision. Thus, instruments used in such procedures are typically long and narrow while being functionally controllable from a proximal end of the instrument.

Significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

An example of a surgical stapler suitable for endoscopic applications is described in U.S. Pat. Appl. Pub. No. US 2004/0232196 A1, the disclosure of which is hereby incorporated by reference in its entirety. The disclosed surgical stapling and severing instrument enables a clinician to close the jaw members upon tissue to position the tissue prior to firing. Once the clinician has determined that the jaw members are properly gripping tissue, the clinician can then fire the surgical stapler to sever and staple the tissue. The simultaneous severing and stapling avoids complications that may arise when performing such actions sequentially with different surgical tools that respectively only sever or staple. In addition, a retraction spring assists in retracting firing components so that the jaws may be unclamped to release the stapled and severed tissue portions.

Thus, while such surgical staplers have provided a significant advancement in surgical procedures, further features would be desirable, such as reducing the force to fire. The requirement of a higher force to operate the trigger may be inconvenient or difficult for a surgeon with limited hand strength. One successful approach to lowering the force to fire is utilizing multiple firing strokes, as described in U.S. patent application Ser. No. 11/052,632, entitled "MULTI-STROKE MECHANISM WITH AUTOMATED END OF STROKE RETRACTION", to Swayze et al., filed 7 Feb. 2005, the disclosure of which is hereby incorporated by reference in its entirety. However, it may be desirable in some instances to retain the simplicity of a single firing stroke, or to reduce force to fire during each stroke of multiple firing strokes.

Consequently, a significant need exists for an improved surgical stapling and severing instrument that effectively severs and staples tissue, but with a reduced amount of force required to pull a firing trigger to cause the severing and stapling.

BRIEF SUMMARY OF THE INVENTION

The invention overcomes the above-noted and other deficiencies of the prior art by providing a surgical instrument that performs a surgical procedure by firing a firing member through an elongate implement portion. This firing motion occurs by the action of a firing actuator moved by the surgeon. The surgeon is assisted by preloading an assistance mechanism in a handle of the surgical instrument, perhaps by a surgical nurse during the preparation of the surgical procedure. This preload bias, which is either toward firing or toward retraction, is coupled to the firing member when the firing member is to move in a firing direction or a retracting direction, respectively.

In one aspect of the invention, a surgical instrument has an assistance mechanism with a follower member proximate and aligned for movement between an unfired and fired positions of a proximal portion of a firing drive train in a handle. A biasing member urges the follower member in a selected direction between unfired and fired positions after being preload by the movement of the shuttle in the opposite direction. An engagement mechanism releases the follower member, which is preload by the biasing member and engaged to the proximal portion of the firing mechanism. The release is in response to the proximal portion of the firing mechanism being moved in the selected direction.

In another aspect of the invention, a surgical instrument includes a proximal portion of a firing mechanism that is held in place by a brake of an engagement mechanism when a follower member is moved from a fired position to an unfired position, which preloads a biasing member in the opposite direction, and engages the biased follower member to the firing mechanism. Firing of the firing mechanism releases the brake to enable assisted firing. Thereby, an effective firing of the implement portion is achieved even if high firing forces are required and the surgeon has limited strength to move the firing mechanism to achieve the required firing forces.

In yet another aspect of the invention, a surgical instrument incorporates preloading of a retraction assistance mechanism that is disengaged during firing to reduce opposition to firing, yet readily engages after firing to retract the firing member through the elongate implement portion.

These and other objects and advantages of the present invention shall be made apparent from the accompanying drawings and the description thereof.

DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 1 depicts a right side view in elevation of a surgical stapling and severing instrument in an open position with an open end effector (staple applying assembly), partially cut away elongate shaft and a firing assistance mechanism.

FIG. 2 depicts a right side view of the open end effector taken in longitudinal cross-section along the lines 2-2 of FIG. 1 of the surgical stapling and severing instrument.

FIG. 35 is a bottom view of the handle of the surgical stapling and severing instrument of FIG. 34 with a left handle housing shell omitted and a bottom portion of a right handle housing shell cut away to expose the wind-up firing assistance mechanism.

FIG. 36 is a bottom detail view of the wind up firing assistance mechanism of FIG. 35.

DETAILED DESCRIPTION OF THE INVENTION

Figure 3:
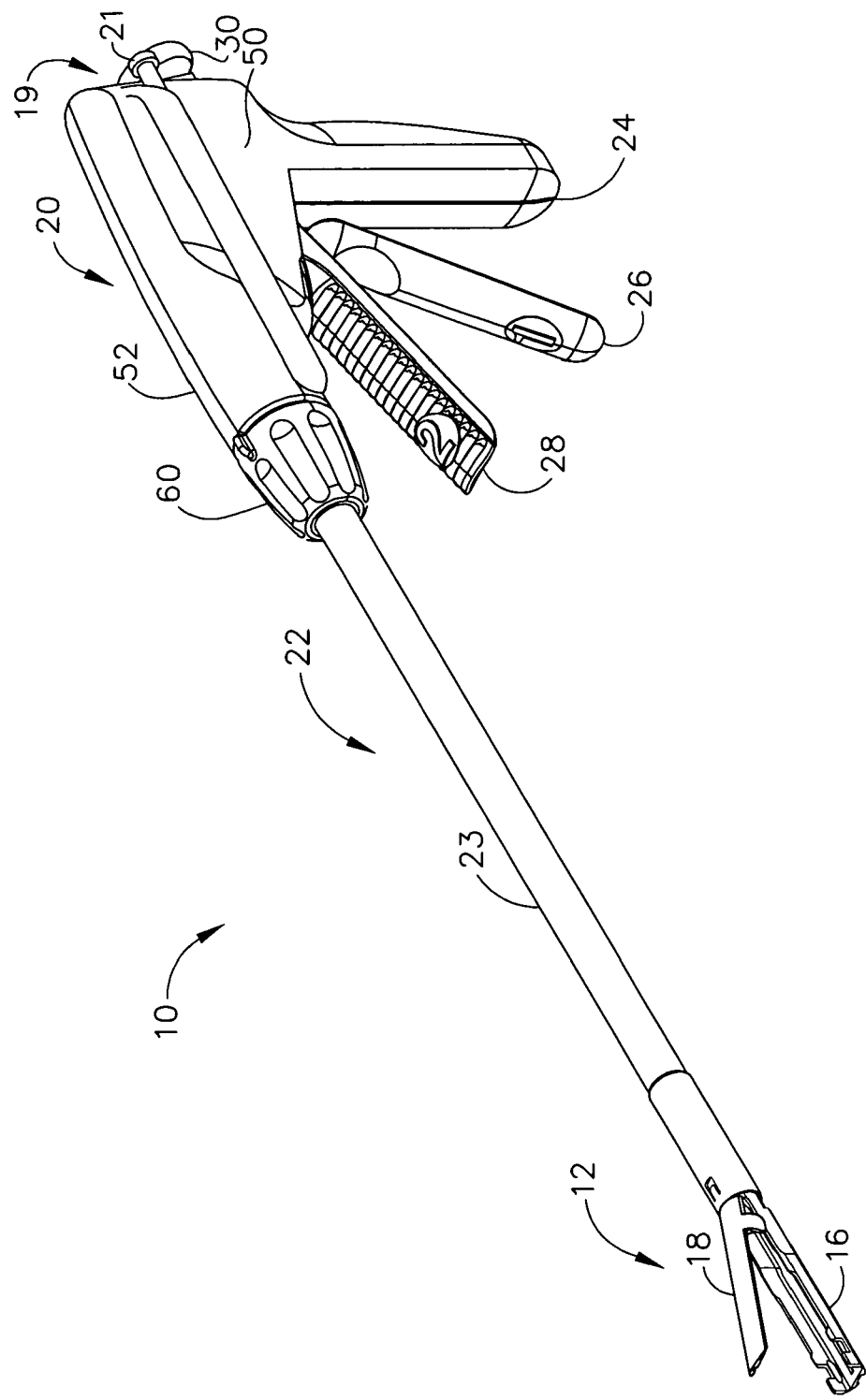
FIG. 3 is a front left isometric view of the surgical stapling and severing instrument of FIG. 1 with a staple cartridge removed.

Turning to the Drawings, wherein like numerals denote like components throughout the several views, in FIG. 1, a surgical stapling and severing instrument 10 is depicted that is capable of practicing the unique benefits of the present invention. The surgical stapling and severing instrument 10 incorporates an end effector 12, which in the illustrative version is a staple applying assembly having an E-beam firing member ("firing bar") 14 (FIG. 2) that controls the spacing of the end effector 12. In particular, an elongate channel 16 and a pivotally translatable anvil 18 are maintained at a spacing that assures effective stapling and severing. Firing this firing bar 14 requires an amount of force to sever tissue, form staples, and to overcome mechanical resistance in the surgical stapling and severing instrument 10. Consistent with aspects of the present invention, an assistance mechanism 19 is incorporated into a handle portion 20 to reduce the amount of force necessarily imparted by the surgeon at the time of firing to achieve this amount of firing force imparted to the firing bar 14. A preloading actuator, depicted as a firing assistance plunger 21 accessible on a left, aft surface of the handle portion 20, allows a surgeon or surgical nurse to prepare the surgical stapling and severing instrument 10 by preloading an amount of mechanical potential energy that subsequently assists in firing.

It will be appreciated that the terms "proximal" and "distal" are used herein with reference to a clinician gripping the handle portion 20 of the surgical stapling instrument 10. Thus, the end effector 12 is distal with respect to the more proximal handle portion 20. The end effector 12 is viewed from the front and the handle portion 20 is viewed from aft. It will be further appreciated that for convenience and clarity, spatial terms such as "vertical" and "horizontal" are used herein with respect to the drawings. However, surgical instruments are used in many orientations and positions, and these terms are not intended to be limiting and absolute.

The surgical and stapling and severing instrument 10 includes an implement portion 22 comprising a shaft 23 proximally attached to the handle portion 20 and distally terminating in the end effector 12. The handle portion 20 includes a pistol grip 24 toward which a closure trigger 26 is pivotally drawn by the clinician to cause clamping, or closing, of the anvil 18 toward the elongate channel 16 of the end effector 12. A firing trigger 28 is farther outboard of the closure trigger 26 and is pivotally drawn by the clinician to cause the stapling and severing of clamped tissue in the end effector 12.

Figure 4:
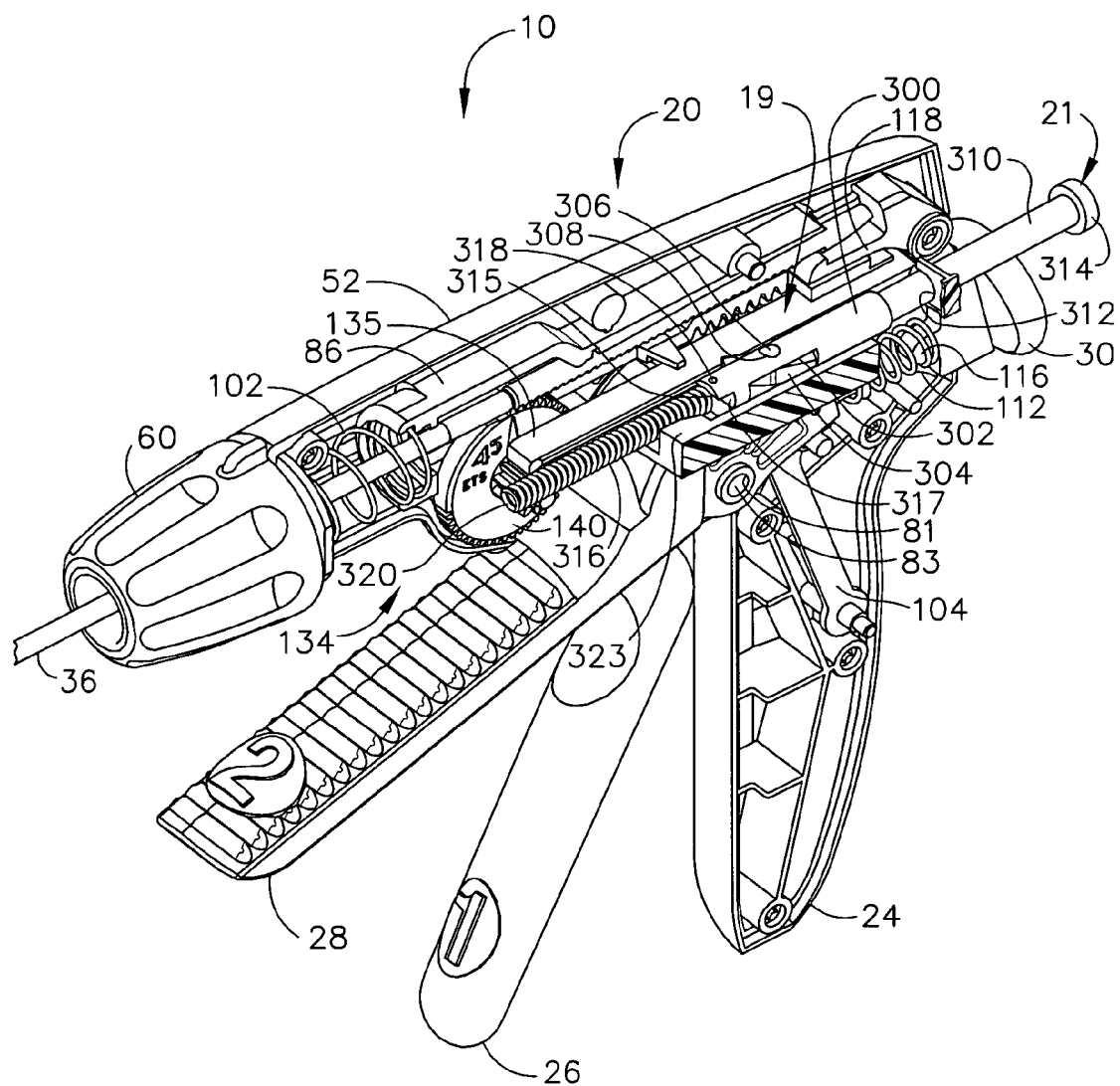
FIG. 4 is a left isometric view of a handle of the surgical stapling and severing instrument of FIG. 1 with a left handle housing shell and firing trigger retraction spring removed to expose a tension-spring firing assistance mechanism in a retracted (preload) state.

In preparation for use, a surgical nurse may draw the firing assistance plunger 21 proximally (aft) until locked into place (FIG. 4). An adjustment knob 29 (FIG. 1) on a right side of the handle portion 20 may be turned to vary that amount of initial force required on the firing trigger 28 to activate the assistance mechanism 19. A desired type of staple cartridge 37 would also be inserted into the end effector 12. The surgeon then depresses the closure trigger 26 to close the end effector 12 and then may position the implement portion 22 through a cannula of a trocar (not shown) to a desired surgical site within the patient's body. Closure trigger 26 is actuated first. Once the clinician is satisfied with the positioning of the end effector 12, the clinician may draw back the closure trigger 26 to its fully closed, clamped position proximate to the pistol grip 24. Then, the firing trigger 28 is actuated. The firing trigger 28 springedly returns when the clinician removes pressure. A release button 30, when depressed on the proximal end of the handle portion 20, releases the clampled closure trigger 26.

The closure motion and firing motion are transferred down the elongate shaft 23. In particular, a closure sleeve 32 encloses a frame 34, which in turn encloses a firing drive rod 36 that is positioned by the firing trigger 28. The frame 34 connects the handle portion 20 to the end effector 12. With the closure sleeve 32 withdrawn proximally by the closure trigger 26 as depicted, the anvil 18 springedly opens, pivoting away from the elongate channel 16 and translating proximally with the closure sleeve 32. The elongate channel 16 receives a staple cartridge 37.

In FIG. 2, the firing bar 14 includes three vertically spaced pins that control the spacing of the end effector 12 during firing. In particular, an upper pin 38 is staged to enter an anvil pocket 40 near the pivot between the anvil 18 and elongate channel 16. When fired with the anvil 18 closed (FIG. 13), the upper pin 38 advances distally within a longitudinal anvil slot 42 extending distally through anvil 18. Any minor upward deflection in the anvil 18 is overcome by a downward force imparted by the upper pin 38. Similarly, if insufficient tissue is clamped, the upper pin 38 may hold up the anvil 18 for proper staple formation. Firing bar 14 also includes a lower most pin, or firing bar cap, 44 that upwardly engages a channel slot 45 in the elongate channel 16, thereby cooperating with the upper pin 38 to draw the anvil 18 and the elongate channel 16 slightly closer together in the event of excess tissue clamped there between or to space part in the event of insufficient tissue. The firing bar 14 includes a middle pin 46 that passes through a firing drive slot 47 formed in a lower surface of the cartridge 37 proximate to an upward surface of the elongate channel 16, thereby driving the staples therein as described below. The middle pin 46, by sliding against a lower surface of the staple cartridge 37 that rests upon the elongate channel 16, resists any tendency for the end effector 12 to be pinched shut at its distal end. A distally presented cutting edge 48 between the upper and middle pins 38, 46 on the firing bar 14 traverses through a proximally presented, vertical slot 49 in the staple cartridge 37 to sever clamped tissue. The affirmative positioning of the firing bar 14 with regard to the elongate channel 16 and anvil 18 assure that an effective cut is performed.

Figure 5:
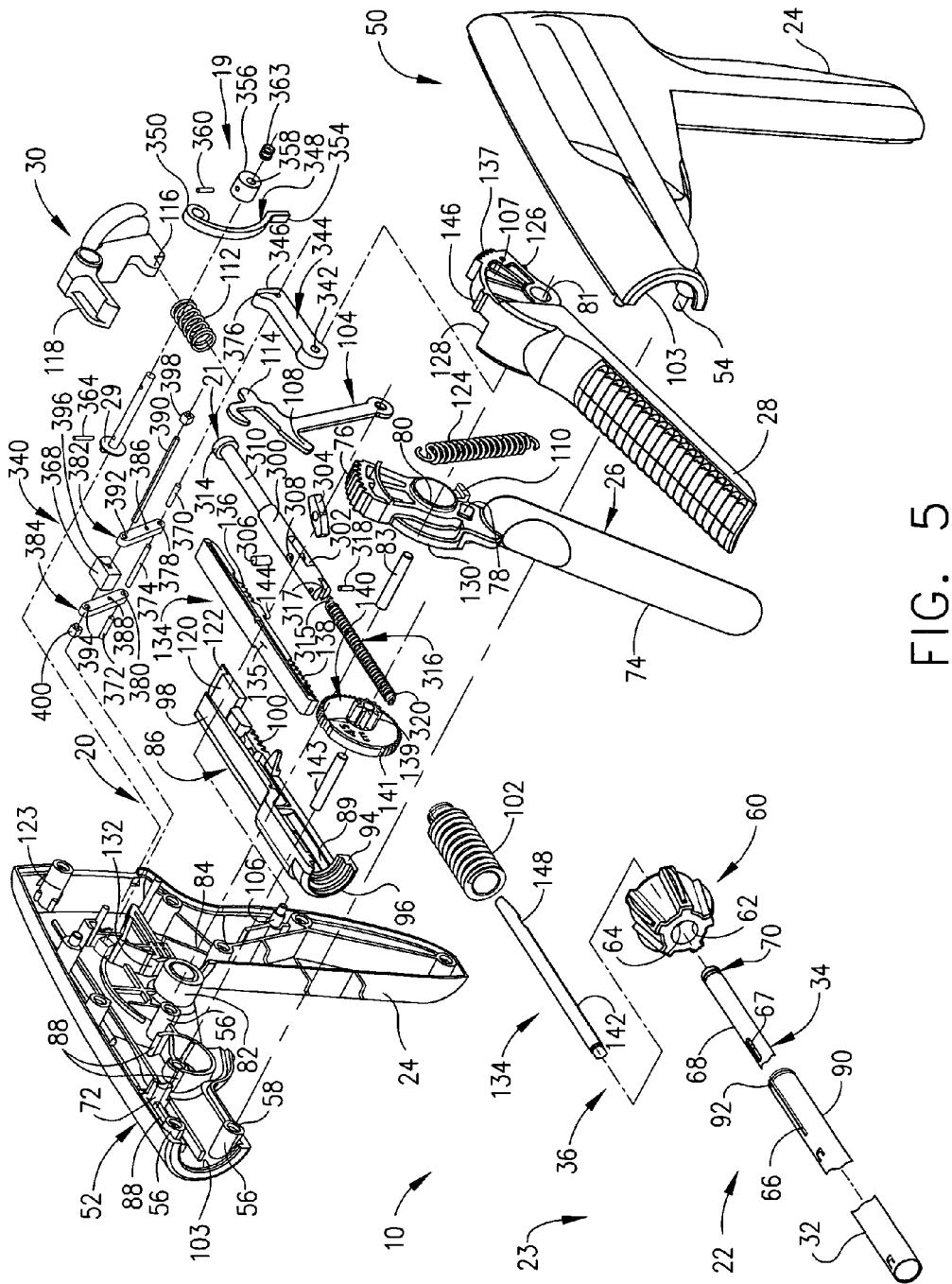
FIG. 5 is a front left isometric view of a disassembled surgical stapling and severing instrument of FIG. 1 with the end effector omitted.

In FIG. 4, the handle portion 20 is partially disassembled from the depiction of FIG. 3 to expose the assistance mechanism 19 that is integrated onto a left side of internal components of the handle portion 20, the latter as described in the U.S. Pat. Appl. Pub. No. US 2004/0232196 A1 cross referenced above. In FIG. 5, the handle portion 20 is fully disassembled. In particular, the handle portion 20 is comprised of left and right handle housing shells 50 and 52, which are molded from a polymeric material such as a glass-filled polycarbonate. The left handle housing shell 50 is provided with a plurality of cylindrical-shaped pins 54. The right handle housing shell 52 includes a plurality of extending members 56, each having a hexagonal-shaped opening 58. The cylindrical-shaped pins 54 are received within the hexagonal-shaped openings 58 and are frictionally held therein for maintaining the left and right handle housing shells 50, 52 in assembly.

With particular reference to FIG. 5, a rotating knob 60 has a bore 62 extending completely through it for engaging and rotating the implement portion 22 about its longitudinal axis. The rotating knob 60 includes an inwardly protruding boss 64 extending along at least a portion of the bore 62. The protruding boss 64 is received within a longitudinal slot 66 formed at a proximal portion of the closure sleeve 32 such that rotation of the rotating knob 60 effects rotation of the closure sleeve 32. It will be appreciated that the boss 64 further extends into a proximal slot 67 in the frame 34 to effect rotation of the elongate shaft 23. Thus, the end effector 12 (FIGS. 1-3) rotates with the rotating knob 60.

A proximal end 68 of the frame 34 passes proximally through the rotating knob 60 and is provided with a circumferential notch 70 that is engaged by opposing channel securement members 72 extending respectively from the left and right handle housing shells 50, 52. Only the channel securement member 72 of the right handle housing shell 52 is shown. The channel securement members 72 extending from the left and right handle housing shells 50, 52 serve to secure the frame 34 to the handle portion 20 such that the frame 34 does not move longitudinally relative to the handle portion 20, but is allowed to rotate about its longitudinal axis.

The closure trigger 26 has a handle section 74, a gear segment section 76, and an intermediate section 78. A bore 80 extends through the intermediate section 78. A cylindrical support member 82 extending from the right handle housing shell 52 passes through the bore 80 for pivotably mounting the closure trigger 26 on the handle portion 20.

In the afore-referenced U.S. Pat. Appl. Pub. No. US 2004/0232196 A1, the firing trigger 28 was pivotally supported upon a second, smaller cylindrical support member that coaxially extends to the left and passes through a bore 81 of firing trigger 28 and into engagement with the left handle housing shell 50 of the handle portion 20 (not shown). Instead, the assistance mechanism 19 advantageously includes a longitudinally movable firing trigger axle 83 that passes though the bore 81 of the firing trigger 28 and its lateral ends slide within longitudinally elongate oval guides 84 formed into both the left and right handle housing shells 50, 52.

A closure yoke 86 is housed within the handle portion 20 for reciprocating movement therein and serves to transfer motion from the closure trigger 26 to the closure sleeve 32. Support members 88, extending from the right handle housing shell 52 and securement member 72, which extends through a recess 89 in the yoke 86, support the yoke 86 within the handle portion 20.

A proximal end 90 of the closure sleeve 32 is provided with a flange 92 that is snap-fitted into a receiving recess 94 formed in a distal end 96 of the yoke 86. A proximal end 98 of the yoke 86 has a gear rack 100 that is engaged by the gear segment section 76 of the closure trigger 26. When the closure trigger 26 is moved toward the pistol grip 24 of the handle portion 20, the yoke 86 and, hence, the closure sleeve 32 move distally, compressing a spring 102 positioned between a distal narrowed ring 103 defined in the left and right handle housing shells 50, 52 and the distal end 96 of the closure yoke 86, that biases the yoke 86 proximally. Distal movement of the closure sleeve 32 effects pivotal translation movement of the anvil 18 distally and toward the elongate channel 16 of the end effector 12 and proximal movement effects closing, as discussed below.

The closure trigger 26 is forward biased to an open position by a front surface 130 interacting with an engaging surface 128 of the firing trigger 28. Clamp first hook 104 that pivots top to rear in the handle portion 20 about a pin 106 restrains movement of the firing trigger 28 toward the pistol grip 24 until the closure trigger 26 is clamped to its closed position. Hook 104 restrains firing trigger 28 motion by engaging a lockout pin 107 in firing trigger 28. The hook 104 is also in contact with the closure trigger 26. In particular, a forward projection 108 of the hook 104 engages a member 110 on the intermediate section 78 of the closure trigger 26, the member 110 being outward of the bore 80 toward the handle section 74. Hook 104 is biased toward contact with member 110 of the closure trigger 26 and engagement with lockout pin 107 in firing trigger 28 by a release spring 112. As the closure trigger 26 is depressed, the hook 104 is moved top to rear, compressing the release spring 112 that is captured between a rearward projection 114 on the hook 104 and a forward projection 116 on the release button 30.

Figure 7:
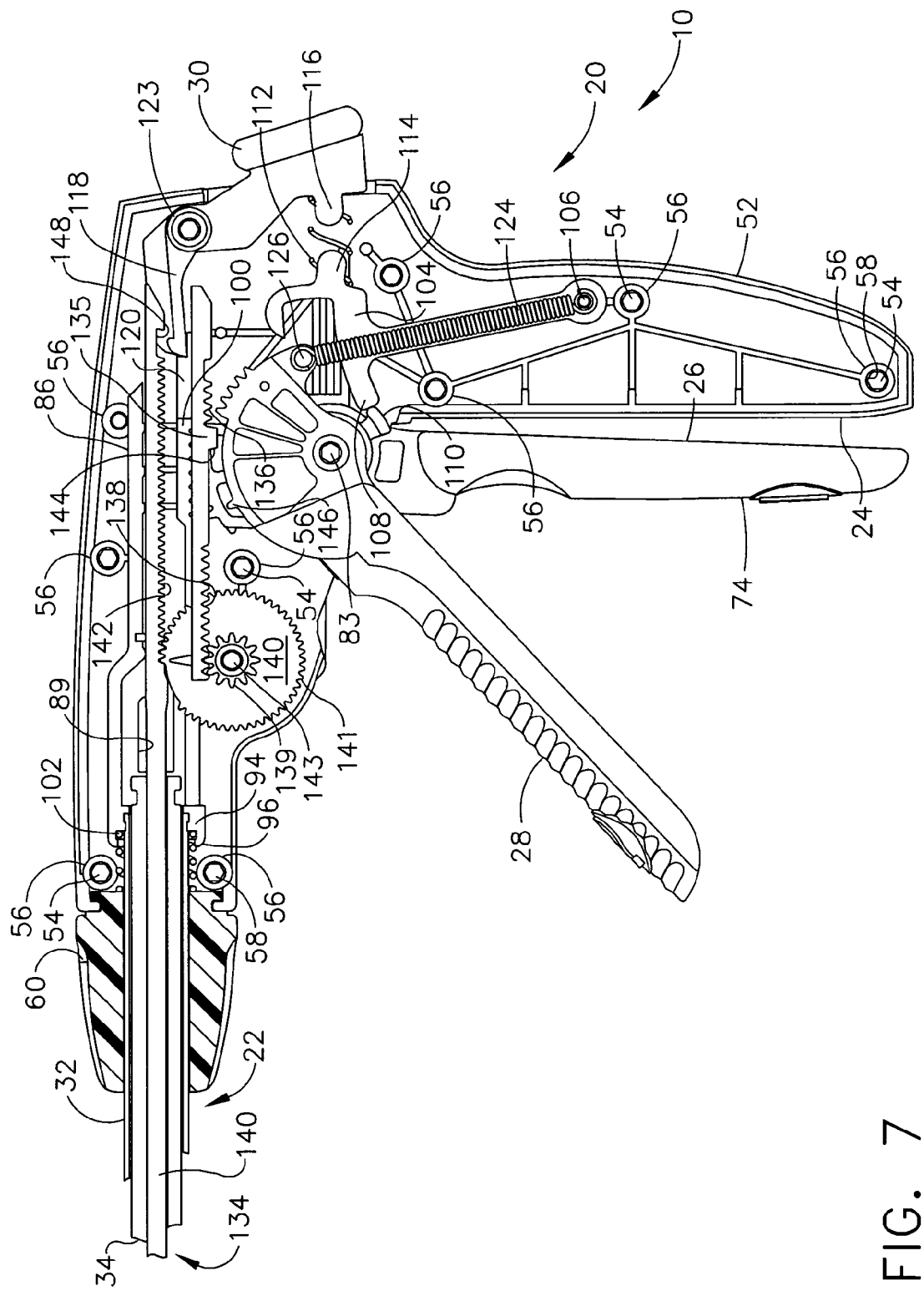
FIG. 7 depicts a left side elevational view of the handle of the surgical stapling and severing instrument of FIG. 1 with the left handle housing shell and assistance mechanism removed to expose interior closure and firing components in a "clamped" position.

As the yoke 86 moves distally in response to proximal movement of the closure trigger 26, an upper latch arm 118 of the release button 30 moves along a proximal, upper surface 120 on the yoke 86 until dropping into an upwardly presented recess 122 in a proximal, lower portion of the yoke 86. The release spring 112 urges the release button 30 outward, which pivots the upper latch arm 118 downwardly into engagement with the upwardly presented recess 122, thereby locking the closure trigger 26 in a tissue clamping position, such as depicted in FIG. 7.

Returning to FIG. 5, the latch arm 118 can be moved out of the recess 122 to release the anvil 18 by pushing the release button 30 inward. Specifically, the upper latch arm 118 pivots upward about pin 123 of the right handle housing shell 52. The yoke 86 is then permitted to move proximally in response to return movement of the closure trigger 26.

A firing trigger return spring 124 is located within the handle portion 20 with one end attached to pin 106 of the right handle housing shell 52 and the other end attached to a pin 126 on the firing trigger 28. The firing return spring 124 applies a return force to the pin 126 for biasing the firing trigger 28 in a direction away from the pistol grip 24 of the handle portion 20. The closure trigger 26 is also biased away from pistol grip 24 by engaging surface 128 of firing trigger 28 biasing front surface 130 of closure trigger 26.

As the closure trigger 26 is moved toward the pistol grip 24, its front surface 130 engages with the engaging surface 128 on the firing trigger 28 causing the firing trigger 28 to move to its "firing" position. When in its firing position, the firing trigger 28 is located at an angle of approximately 45° to the pistol grip 24. After staple firing, the spring 124 causes the firing trigger 28 to return to its initial position. During the return movement of the firing trigger 28, its engaging surface 128 pushes against the front surface 130 of the closure trigger 26 causing the closure trigger 26 to return to its initial position. A stop member 132 extends from the right handle housing shell 52 to prevent the closure trigger 26 from rotating beyond its initial position.

The surgical stapling and severing instrument 10 additionally includes a firing reciprocating assembly ("firing drive train") 134 that transfers firing motions from the firing trigger 28 to the end effector 12 for severing and stapling tissue. Although a separate closure approach is incorporated in the illustrative version, applications consistent with the present invention may use a first portion of the distal travel of the firing drive train 134 to close the end effector 12 with the later portions of the distal travel used to sever and staple. A proximal portion of the firing drive train 134 is received within the handle portion 20 and a distal portion of the firing drive train 134 is received within the implement portion 22. The proximal portion of the firing drive train 134 begins with a longitudinally elongate rectangular plate 135 having a proximal gear rack segment 136 that engages to a gear segment 137 upwardly presented on the firing trigger 28 above the pivot axis defined by the bore 81 and firing trigger axle 83. A distal gear rack segment 138 on the rectangular plate 135 engages a leftward small spur gear (pinion) 139 of a coaxial dual spur gear (multiplier gear) 140, which freewheels on a laterally aligned gear axle 143 and whose large spur gear (large pinion) 141 engages a rod gear rack 142 formed on a proximal end of the firing drive rod 36. The firing rod 36 and firing bar 14 thus form the distal portion of the firing drive train 134 that transfer this firing motion through the implement portion 22.

A first notch 144 is provided on the rectangular plate 135 intermediate the proximal and distal gear rack segments 136, 138. During return movement of the firing trigger 28, a tooth 146 on the firing trigger 28 engages with the first notch 144 on the rectangular plate 135 for returning the rectangular plate 135 to its initial position after staple firing. A second notch 148 is located at a proximal end of the firing drive rod 36 for locking the firing drive rod 36 to the upper latch arm 118 of the release button 30 in its unfired position.

Figure 6:
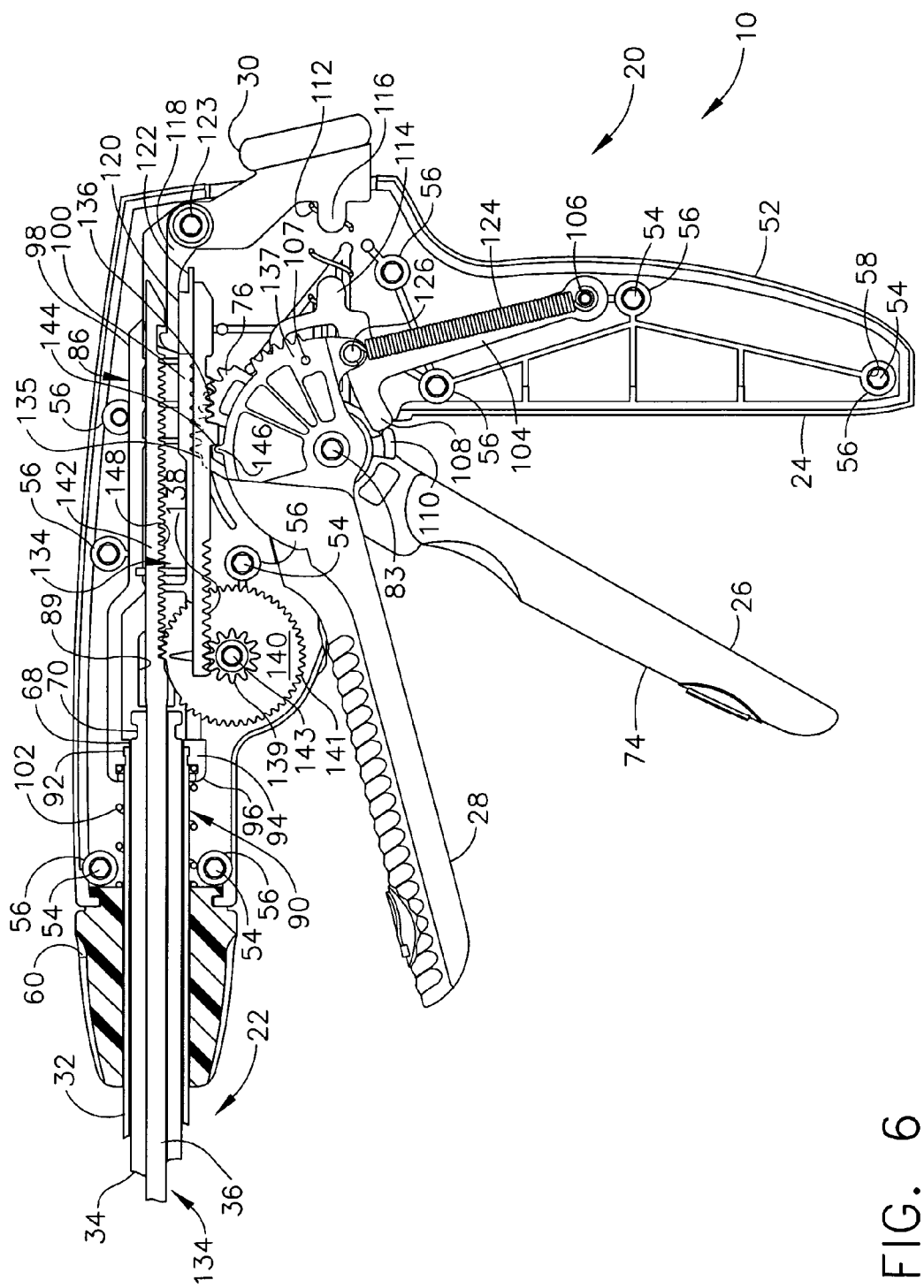
FIG. 6 depicts a left side elevational view of the handle portion of the surgical stapling and severing instrument of FIG. 1 with a left handle housing shell and assistance mechanism removed to expose interior closure and firing components in an unclamped, unfired ("start") position.
Figure 8:
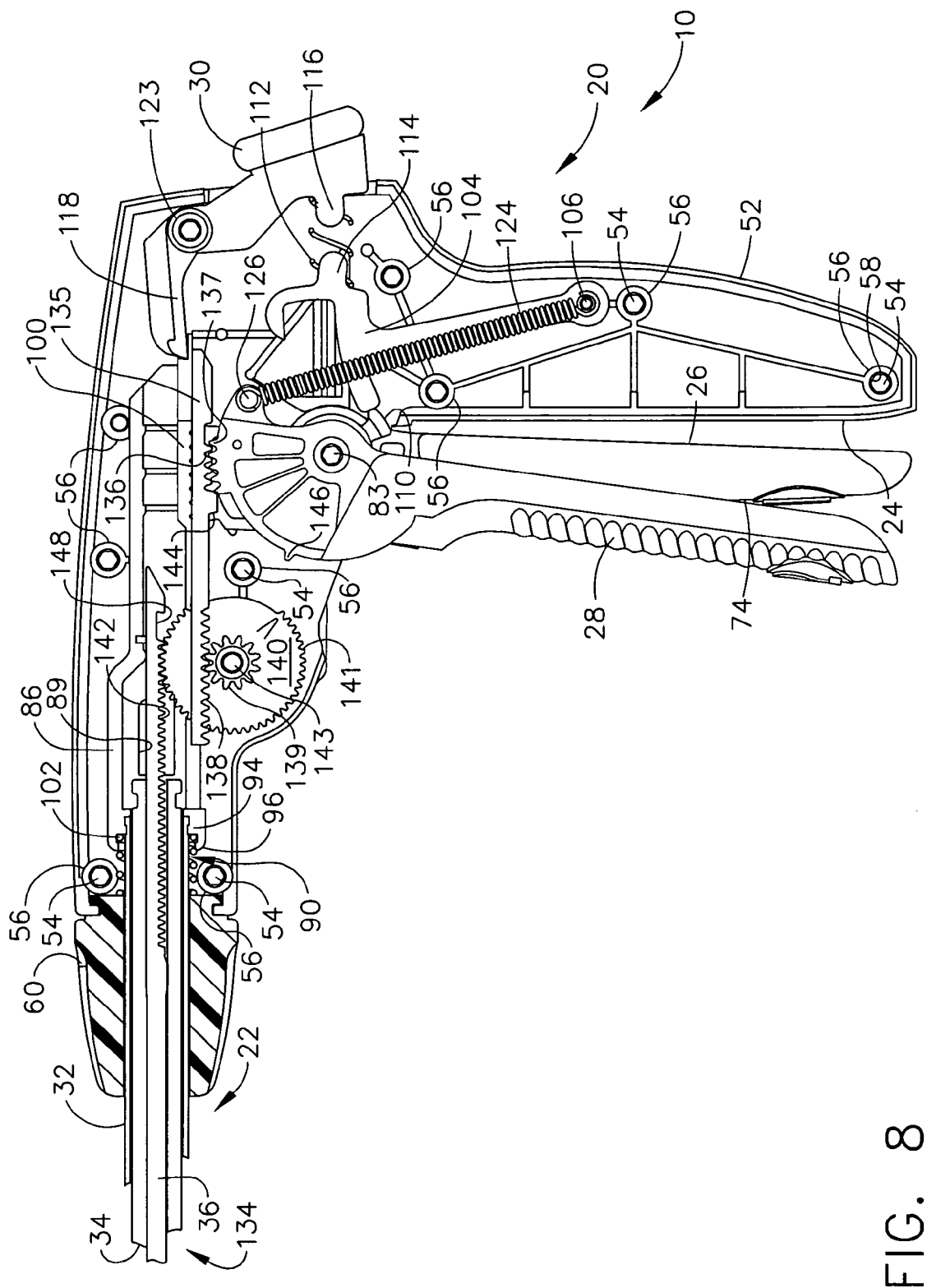
FIG. 8 depicts a left side elevational view of the handle of the surgical stapling and severing instrument of FIG. 1 with the left handle housing shell and assistance mechanism removed to expose interior closure and firing components in the stapled and severed ("fired") position.

Before describing the components and operation of the assistance mechanism 19, in FIGS. 6-8, the handle portion 20 is depicted with the left handle housing shell 50 and the assistance mechanism 19 removed for clarity in describing the closure and firing components. In FIG. 6, the handle portion 20 is in the start position (open and unfired). In FIG. 7, the handle portion 20 is in a clamped position (closed and unfired). In FIG. 8, the handle portion is in a fired position. In order to prevent staple firing before tissue clamping has occurred, the upper latch arm 118 on the release button 30 is engaged with the second notch 148 on the rectangular plate 135 such that the firing drive rod 36 is locked in its proximal-most position, as depicted in FIG. 6. When the upper latch arm 118 falls into the recess 122, the upper latch arm 118 disengages with the second notch 148 to permit distal movement of the firing drive rod 36, as depicted in FIG. 8.

Because the distal gear rack segment 138 on the rectangular plate 135 and the rod gear rack 142 on the firing drive rod 36 are engaged with the multiplier gear 140, movement of the firing trigger 28 causes the firing drive rod 36 to reciprocate between a first reciprocating position, shown in FIG. 7, and a second reciprocating position, shown in FIG. 8. Since the diameter of the large pinion gear 141 is greater than the diameter of the small pinion gear 139, the multiplier gear 140 moves the distal portion of the firing drive train 134 (i.e., firing drive rod 36 and firing bar 14) a greater distance than the rectangular plate 135 is moved by the firing trigger 28. The relative diameters of the larger and small pinion gears 139, 141 may be selected to permit the length of the stroke of the firing trigger 28 and the force required to move it to be varied.

The end effector 12 of the surgical stapling and severing instrument 10 is depicted in further detail in FIGS. 9-15. As described above, the handle portion 20 produces separate and distinct closing and firing motions that actuate the end effector 12. The end effector 12 maintains the clinical flexibility of this separate and distinct closing and firing (i.e., stapling and severing). In addition, the end effector 12 introduces the aforementioned ability to affirmatively maintain the closed spacing during firing after the clinician positions and clamps the tissue. Both features procedurally and structurally enhance the ability of the surgical stapling and severing instrument 10 by ensuring adequate spacing for instances where an otherwise inadequate amount of tissue is clamped and to enhance the clamping in instances where an otherwise excessive amount of tissue has been clamped.

Figure 9:
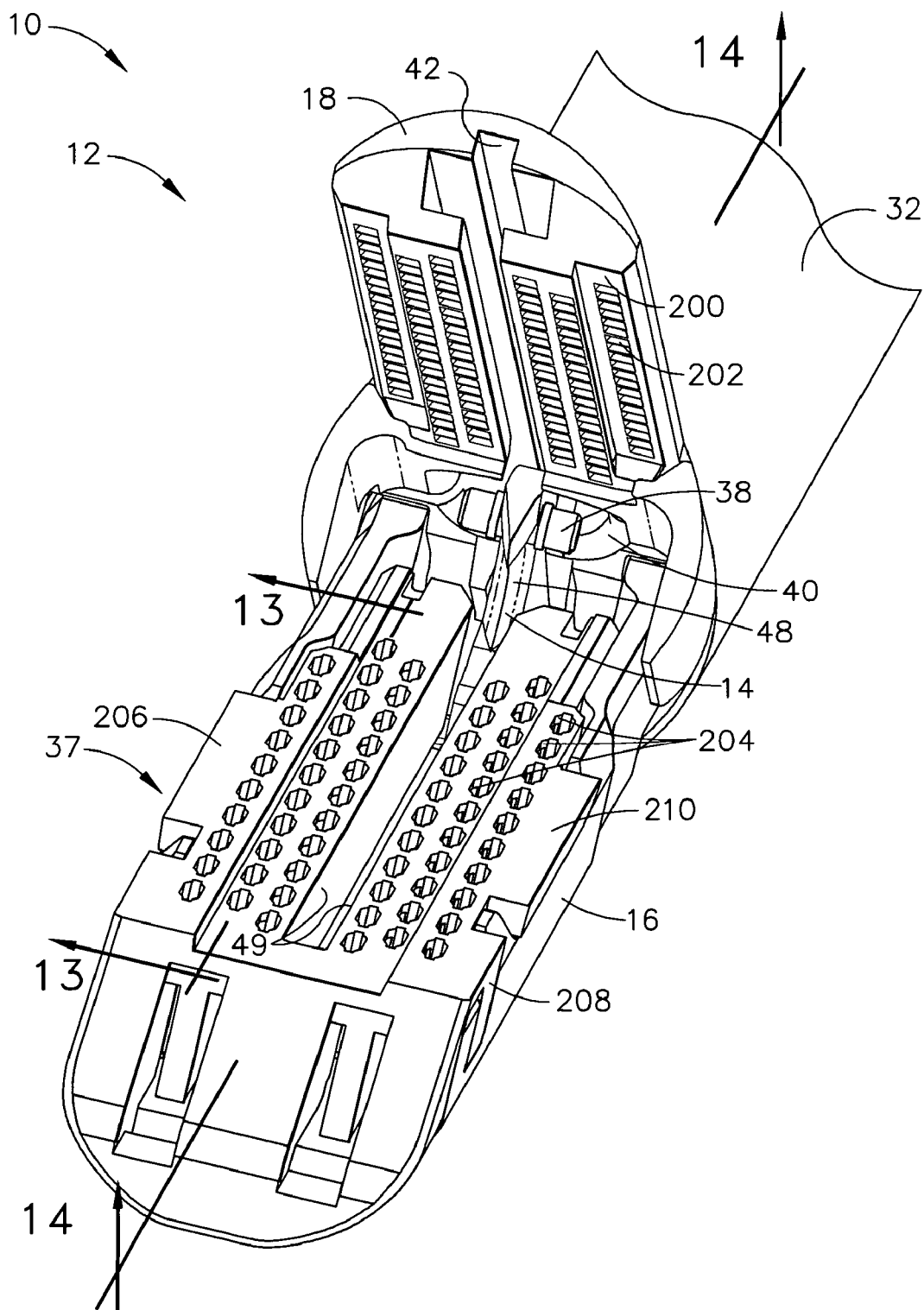
FIG. 9 depicts an isometric view of the end effector at the distal end of the surgical stapling and severing instrument of FIG. 1 with the anvil in the up or open position exposing the staple cartridge and cutting edge of a firing bar.

In FIG. 9, the end effector 12 is in an open position by a retracted closure sleeve 32 and includes a staple cartridge 37 installed in the elongate channel 16. On a lower surface 200 of the anvil 18, a plurality of stapling forming pockets 202 are arrayed to correspond to a plurality of stapler apertures 204 in an upper surface 206 of the staple cartridge 37. The firing bar 14 is at its proximal position, with the upper pin 38 aligned in a noninterfering fashion with the anvil pocket 40. The anvil pocket 40 is shown as communicating with the longitudinal anvil slot 42 in the anvil 18. The distally presented cutting edge 48 of the firing bar 14 is aligned with and proximally from removed from the vertical slot 49 in the staple cartridge 37, thereby allowing removal of a spent cartridge and insertion of an unfired cartridge, which is snapfit into the elongate channel 16. Specifically, extension features 208, 210 of the staple cartridge 37 engage recesses 212, 214 (shown in FIG. 11) of the elongate channel 16.

Figure 10:
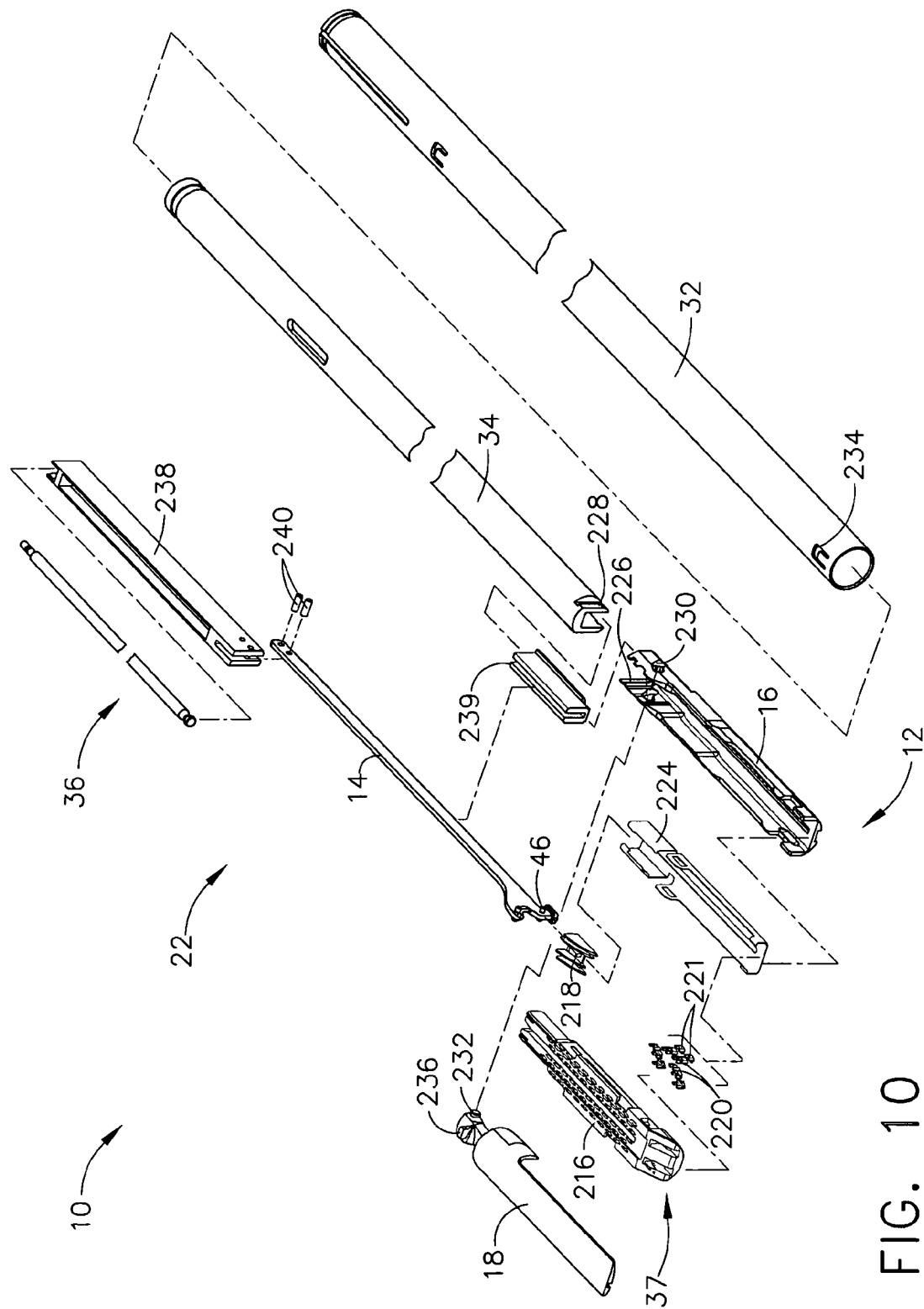
FIG. 10 depicts an isometric, exploded view of the implement portion of the surgical stapling and severing instrument of FIG. 1.

In FIG. 10, the implement portion 22 of the surgical stapling and severing instrument 10 is in disassembled form. The staple cartridge 37 is shown as being comprised of a cartridge body 216, a wedge sled 218, single and double drivers 220, 221 staples 222 (FIGS. 13, 15), and a cartridge tray 224. When assembled, the cartridge tray 224 holds the wedge sled 218, single and double drivers 220, 221 and staples 222 inside the cartridge body 216.

Having a wedge sled 218 integral to the staple cartridge 37 enables a number of flexible design options as compared to incorporating camming surfaces onto a firing bar itself. For instance, a number of different staple cartridges 37 may be selected for use in the surgical stapling and severing instrument 10 with each staple cartridge 37 having a different configuration of rows of staples 222, each thus having a unique wedge sled 218 configured to contact the middle pin 46 of the firing bar 14 while causing the driving of the staples 222. As another example, the integral wedge sled 218 provides an opportunity for a number of lockout features.

The elongate channel 16 has a proximally placed attachment cavity 226 that receives a channel anchoring member 228 on the distal end of the frame 34 for attaching the end effector 12 to the handle portion 20. The elongate channel 16 also has an anvil cam slot 230 that pivotally receives an anvil pivot 232 of the anvil 18. The closure sleeve 32 that encompasses the frame 34 includes a distally presented horseshoe shaped aperture 234 that engages an anvil feature 236 proximate but distal to the anvil pivot 232 on the anvil 18 to thereby effect opening and closing of the anvil 18. The firing drive rod 36 is shown as being assembled to the firing bar 14 by a firing connector 238 by pins 240, which in turn is rotatingly and proximally attached to the firing drive rod 36. The firing bar 14 is guided at a distal end of the frame 34 by a slotted guide 239 inserted therein.

Figure 11:
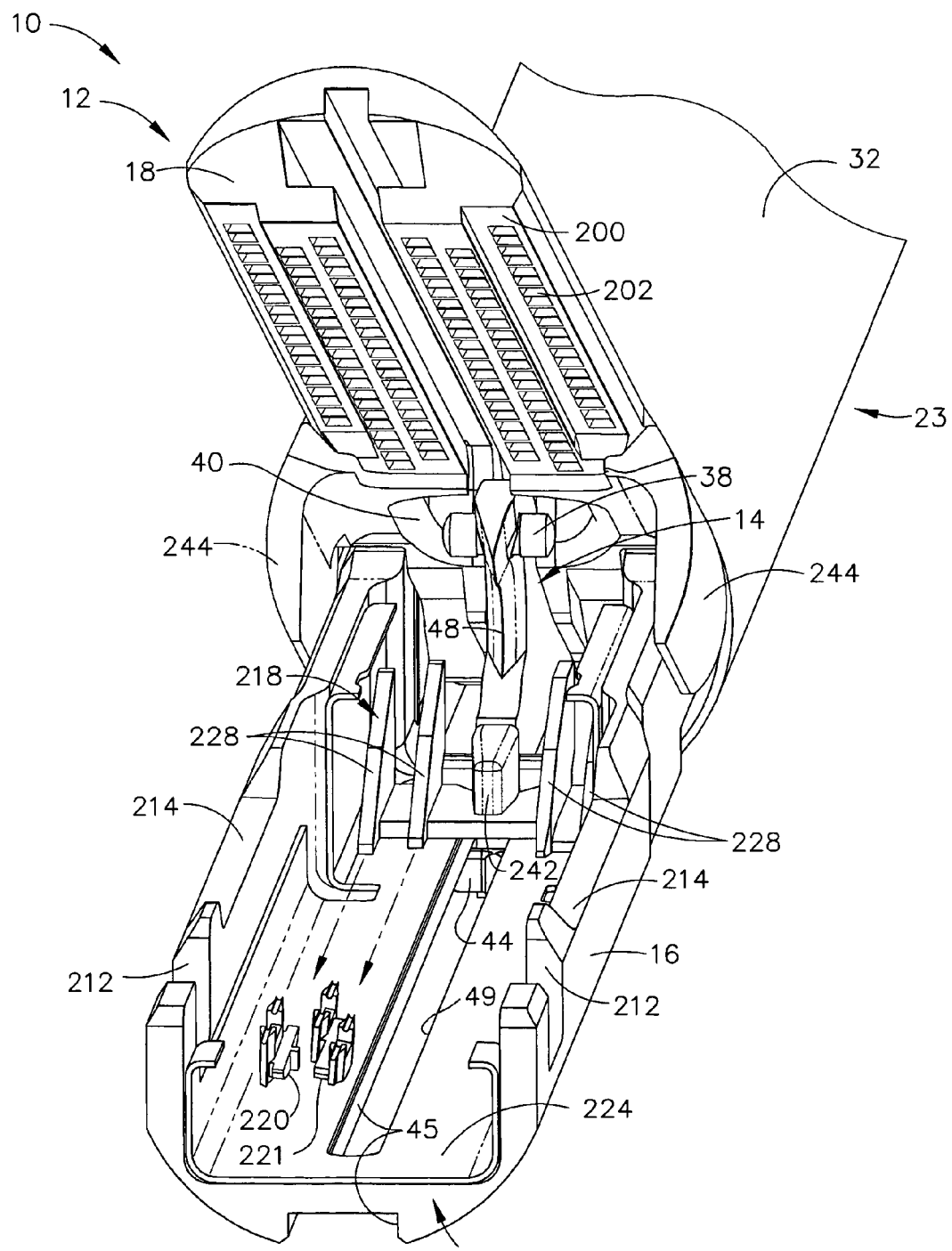
FIG. 11 depicts an isometric view of the end effector at the distal end of the surgical stapling and severing instrument of FIG. 1 with the anvil in the up or open position with the staple cartridge largely removed exposing a single staple driver and a double staple driver as exemplary and a wedge sled in a start position against a middle pin of the firing bar.

With particular reference to FIG. 11, a portion of the staple cartridge 37 is removed to expose portions of the elongate channel 16, such as recesses 212, 214 and to expose some components of the staple cartridge 37 in their unfired position. In particular, the cartridge body 216 (shown in FIG. 10) has been removed. The wedge sled 218 is shown at its proximal, unfired position with a pusher block 242 alligned to contact the middle pin 46 (hidden in FIG. 11) of the firing bar 14. The wedge sled 218 is in longitudinal sliding contact upon the cartridge tray 224 and includes wedges 228 that force upward the single and double drivers 220, 221 as the wedge sled 218 moves distally. Staples 222 (not shown in FIG. 11) resting upon the drivers 220, 221 are thus also forced upward into contact with the anvil forming pockets 202 on the anvil 18 to form closed staples 222. Also depicted is the channel slot 45 in the elongate channel 16 that is aligned with the vertical slot 49 in the staple cartridge 37.

Figure 12:
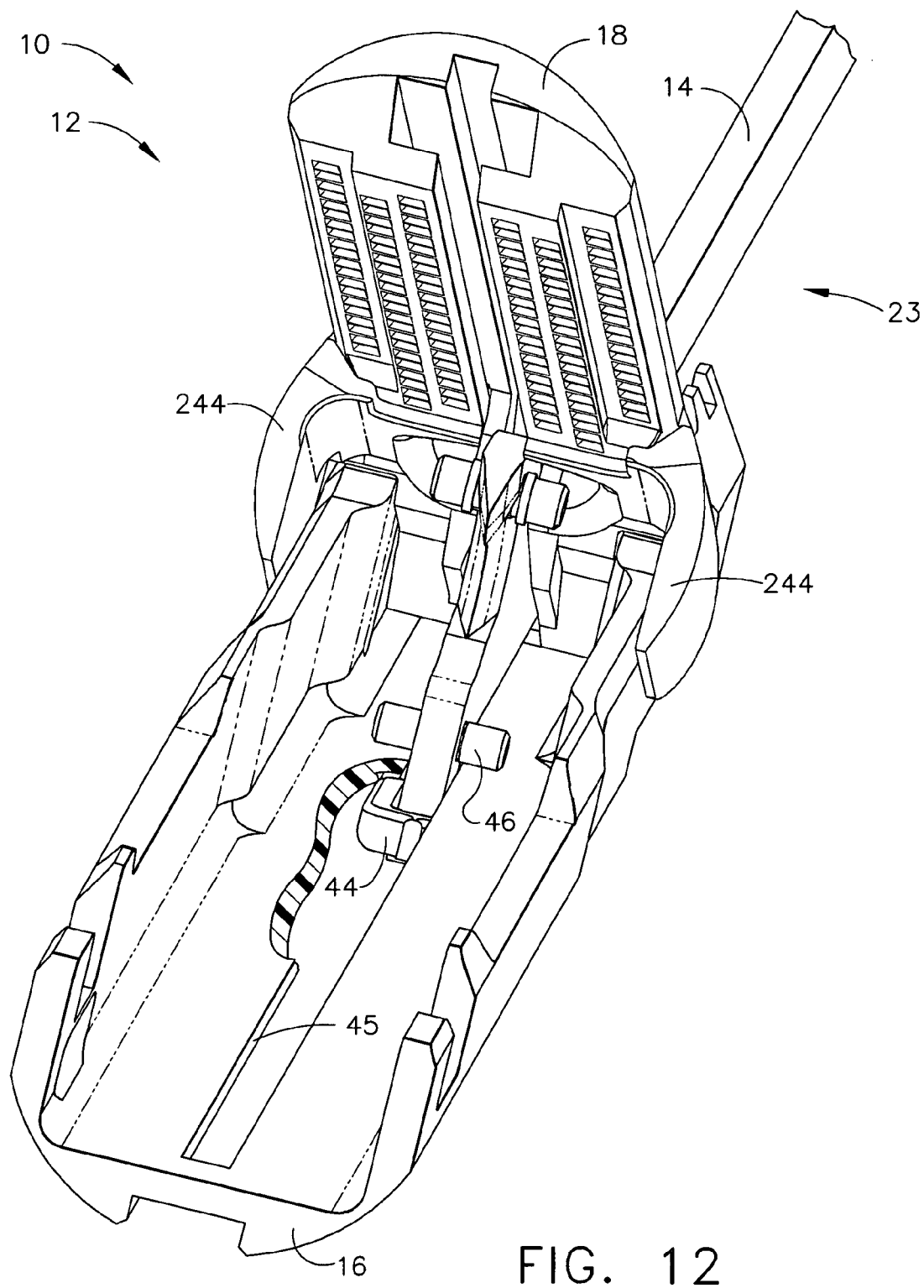
FIG. 12 depicts an isometric view of the distal end of the surgical stapling and severing instrument of FIG. 1 with the anvil in the up or open position with the staple cartridge completely removed and a portion of an elongate channel removed to expose a lowermost pin of the firing bar.

In FIG. 12, the end effector 12 of FIG. 11 is depicted with all of the staple cartridge 37 removed to show the middle pin 46 of the firing bar 14 as well as portion of the elongate channel 16 removed adjacent to the channel slot 45 to expose the firing bar cap 44. In addition, portions of the shaft 23 are removed to expose a proximal portion of the firing bar 14. Projecting downward from the anvil 18 near the pivot, a pair of opposing tissue stops 244 prevent tissue from being positioned too far up into the end effector 12 during clamping.

Figure 13:
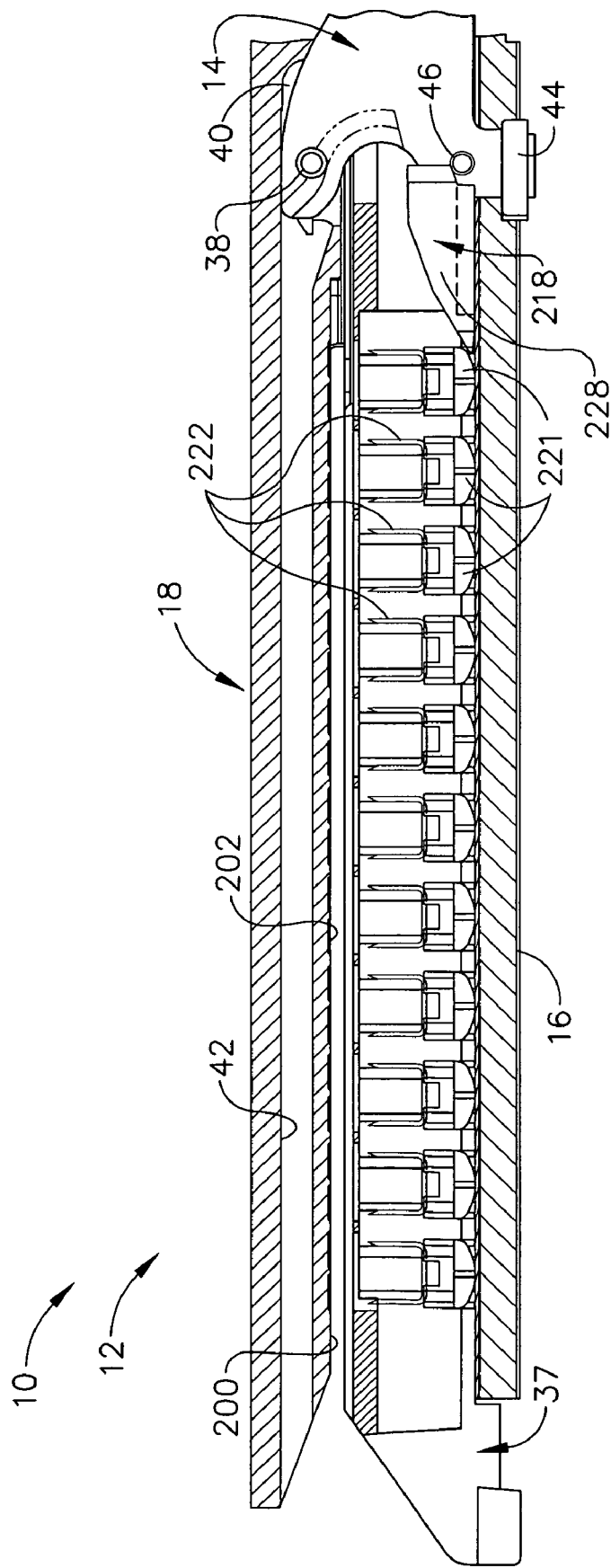
FIG. 13 depicts a side elevation view in section showing a mechanical relationship between the anvil, elongate channel, and staple cartridge in the closed position of the surgical stapling and severing instrument of FIG. 1, the section generally taken along lines 13-13 of FIG. 9 to expose the wedge sled, staple drivers and staples but also depicting the firing bar along the longitudinal centerline.

In FIG. 13, the end effector 12 is closed in a tissue clamping position with the firing bar 14 unfired. The upper pin 38 is in the anvil pocket 40, vertically aligned with the anvil slot 42 for distal longitudinal movement of the firing bar 14 during firing. The middle pin 46 is positioned to push the wedge sled 218 distally so that wedge 228 sequentially contacts and lifts double drivers 221 and the respective staples 222 into forming contact with staple forming pockets 202 in the lower surface 200 of the anvil 18.

Figure 14:
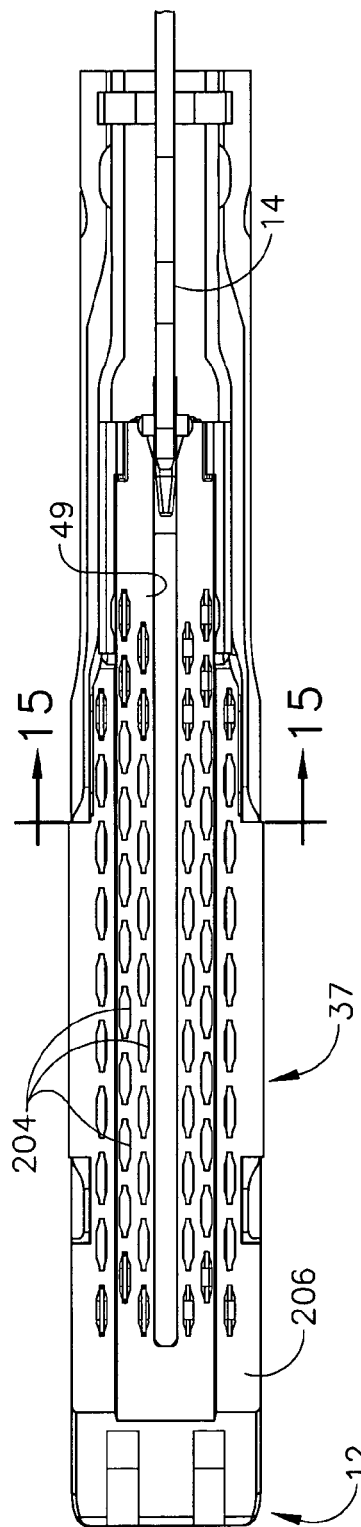
FIG. 14 depicts a section view of the end effector of the surgical stapling and severing instrument with the cartridge and firing bar in the start position taken along line 14-14 of FIG. 9.

In FIG. 14, the upper surface 206 of the staple cartridge 37 is depicted with the firing bar 14 in its unfired, proximal position. The stapler apertures 204 are arrayed on each side of the vertical slot 49 in the staple cartridge 37.

Figure 15:
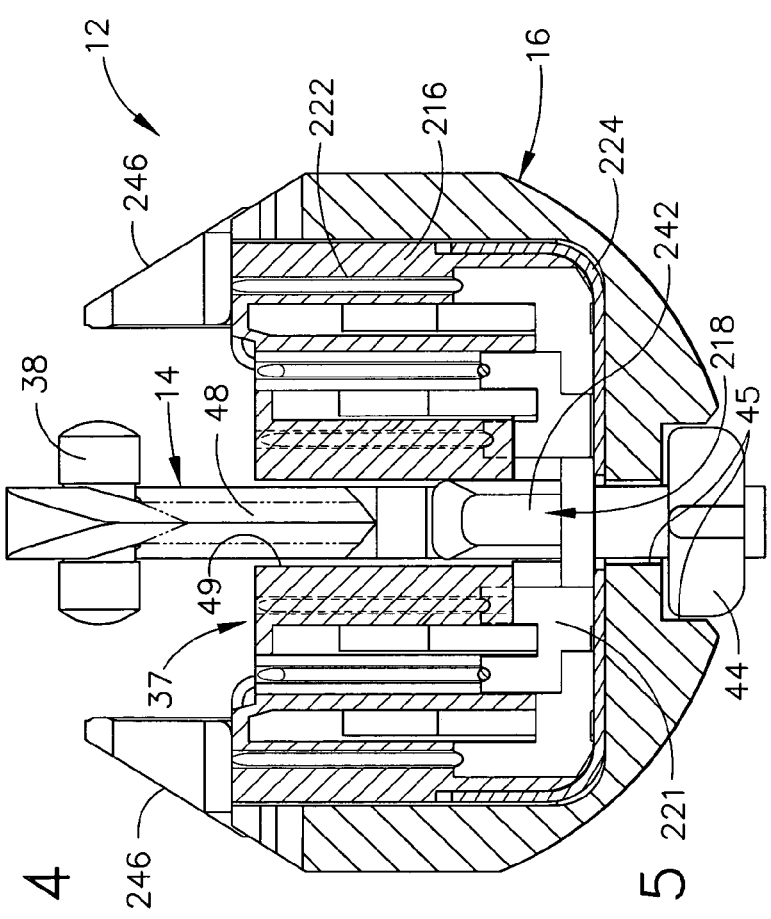
FIG. 15 depicts a section view taken along line 15-15 of FIG. 14 showing the cross-sectional relationship between the firing bar, elongate channel, wedge sled, staple drivers, staples and staple cartridge.

In FIG. 15, the portion of the elongate channel 16 of the end effector 12 near the pivot has opposing ramp portions 246 to thereby cooperate with the tissue stops 244 of the anvil 18 (FIG. 12) to prevent tissue from jamming the end effector 12. Also depicted in greater detail are the double drivers 221 and their relation to the staples 222.

Returning to FIGS. 4-5, the assistance mechanism 19 complements the operation of the afore-described firing components of the handle portion 20 having a spring biased follower member, which in the illustrative version is a linearly moving shuttle 300, that selectively urges a proximal portion of the firing drive train 134, which in the illustrative version is the rectangular plate 135. The shuttle 300 has a lateral through slot 302 in which a cam finger 304 is centrally engaged for horizontal rotation by a vertical pin 306 residing in a pin hole 308. A proximal end of the shuttle 300 is attached to the firing assistance plunger 21 whose cylindrical shaft 310 slides through a plunger hole 312 (FIG. 4) formed in the left handle housing shell 50 (FIG. 5). A stop surface of the plunger 21 is provided by an increased diameter cylindrical finger grip 314 at an aft end of the cylindrical shaft 310. A distal end of the shuttle 300 is attached to a proximal hook end 315 of a tension spring 316 residing with a distally open lateral slot 317 in the shuttle 300 by a pin 318. A distal hook end 320 of the tension spring 316 is attached to a distal portion of the left handle housing shell 50 such that retraction of the plunger 21, as in FIG. 4, stretches the tension spring 316 storing mechanical potential energy therein. A shuttle tray structure 323 formed in the left handle housing shell 50 guides the tension spring 316 and shuttle 300 and limits the distal movement of the shuttle 300 (FIG. 4).

Figure 16:
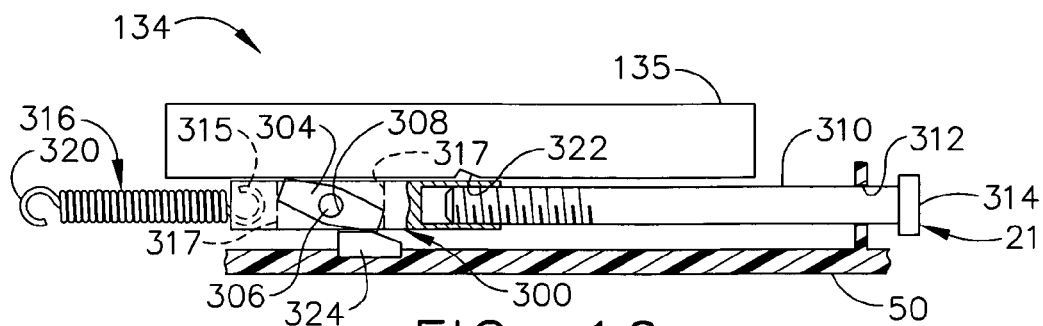
FIG. 16 is a top view of the tension spring firing assistance mechanism of FIG. 4 in an initial, start state with a small rack (rectangular plate of a firing drive train) retracted and an unloaded shuttle.
Figure 17:
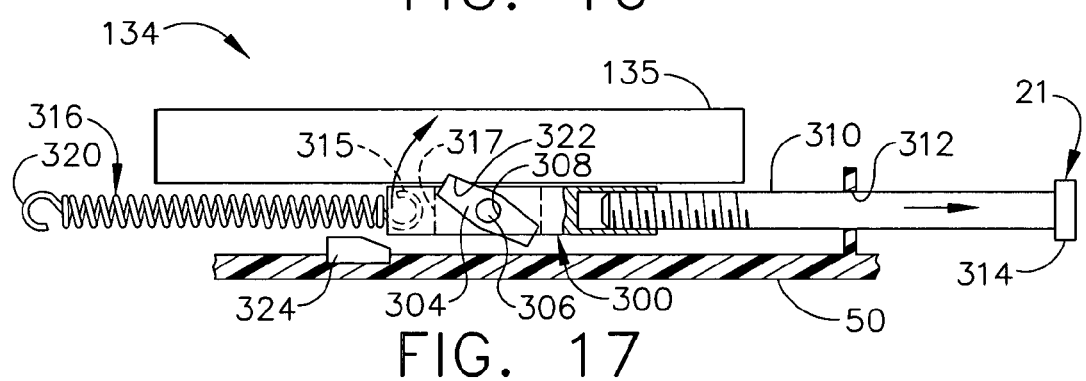
FIG. 17 is a top view of the tension spring firing assistance mechanism of FIG. 16 in an armed state (preload) with the small rack retracted by the shuttle causing an extended tension spring.
Figure 18:
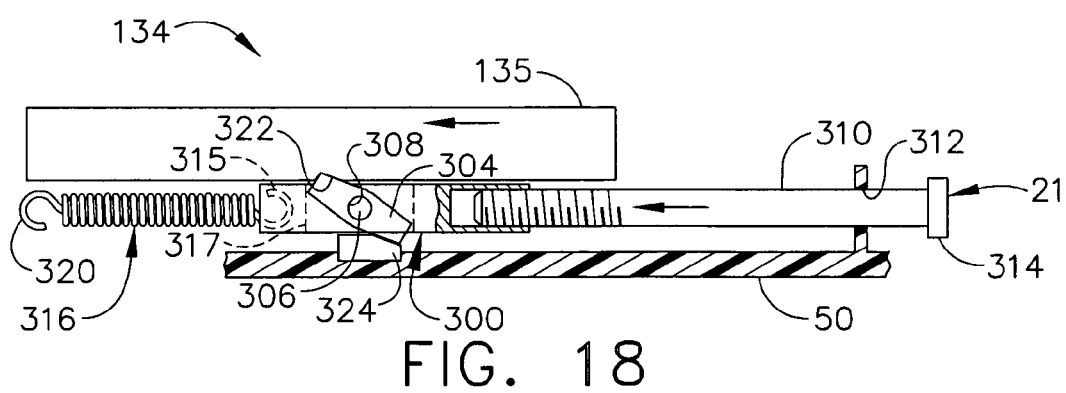
FIG. 18 is a top view of the tension spring firing assistance mechanism of FIG. 17 in a triggered state (firing) with the small rack being distally biased by the extended tension spring via the engaged shuttle while being simultaneously distally advanced by a firing trigger.
Figure 19:
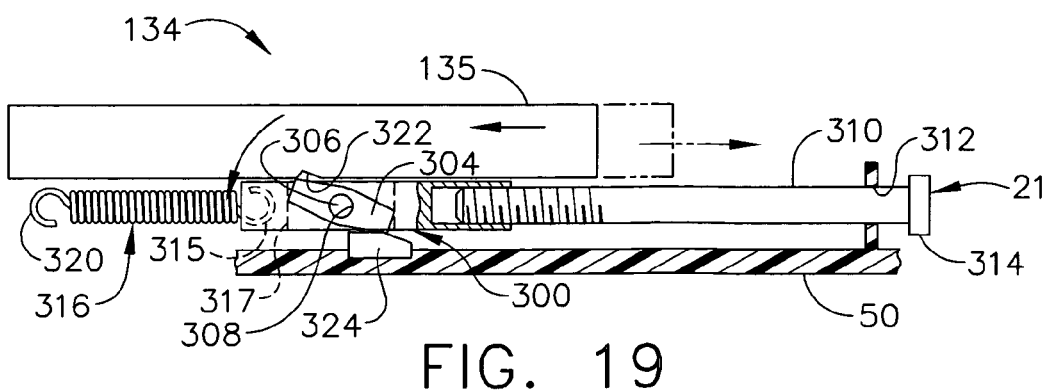
FIG. 19 is a top view of the tension spring firing assistance mechanism of FIG. 18 in a unloaded, fired state with the small rack being proximally retracted to return to the initial state after disengagement from the distally-positioned shuttle.
Figure 20:
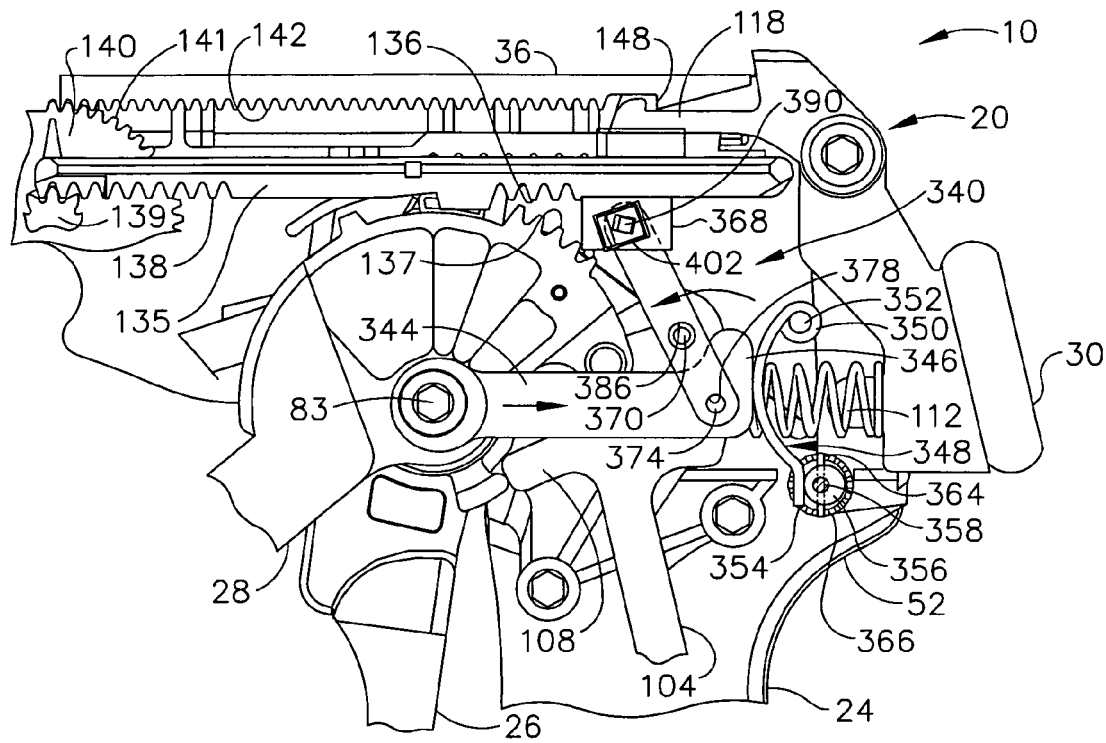
FIG. 20 is a left side view in elevation of a top aft portion of the handle with the left handle housing shell removed from the surgical stapling and severing instrument of FIG. 1 exposing a firing handle being fired to release a small rack brake of the firing assistance mechanism of FIG. 4.
Figure 21:
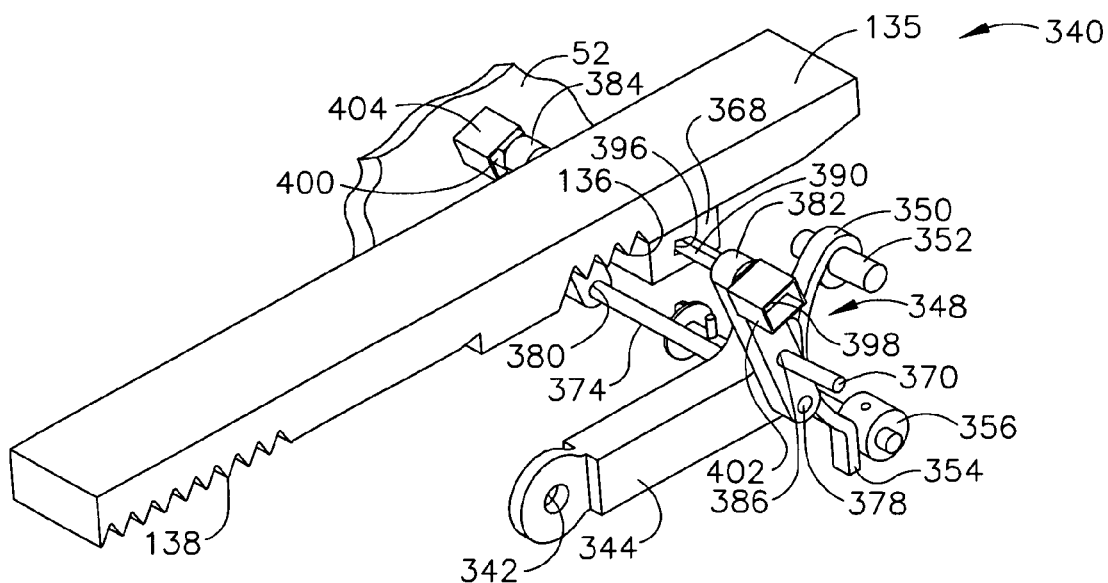
FIG. 21 is a front left isometric view of the small rack and brake assembly of FIG. 20.
Figure 22:
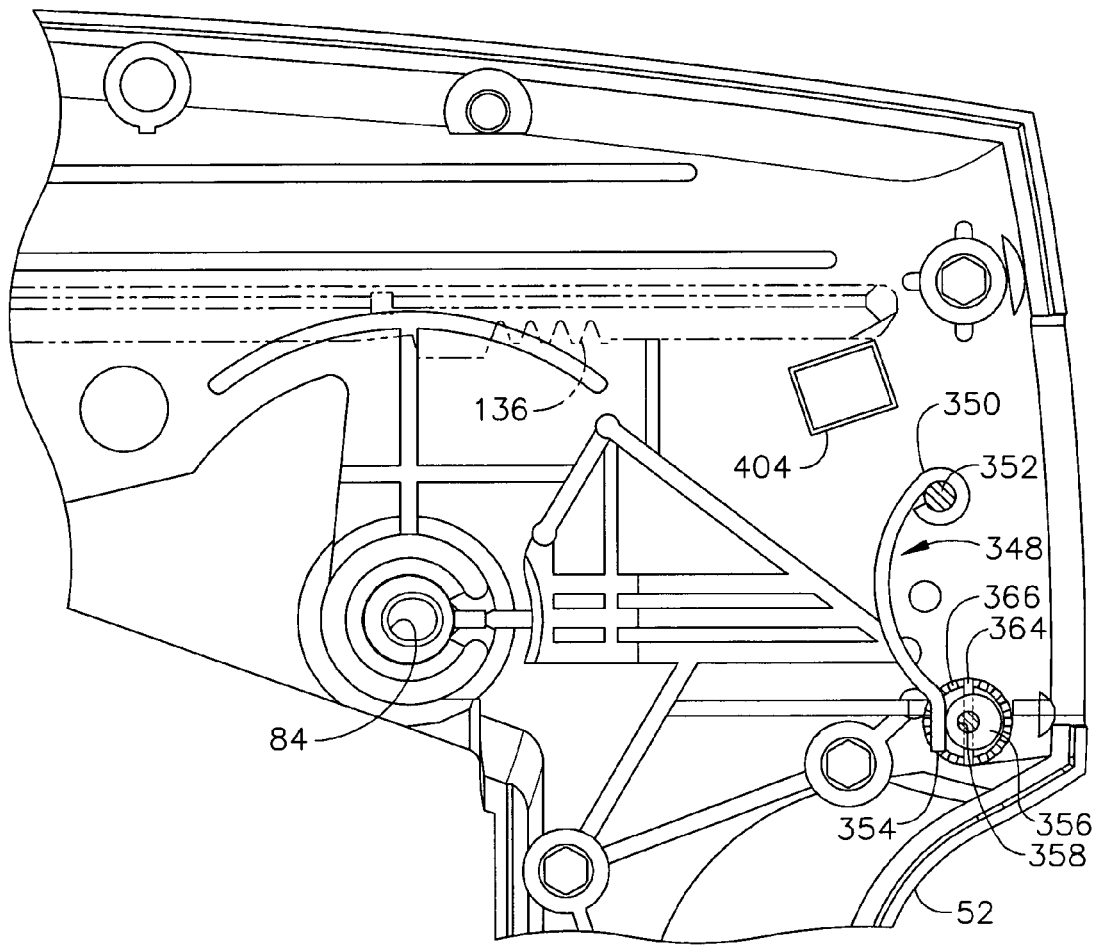
FIG. 22 is a left side view in elevation of a top aft portion of a right handle housing shell having a laterally elongate firing axle slot and an axle bias leaf spring of the firing assistance mechanism of FIG. 4.
Figure 23:
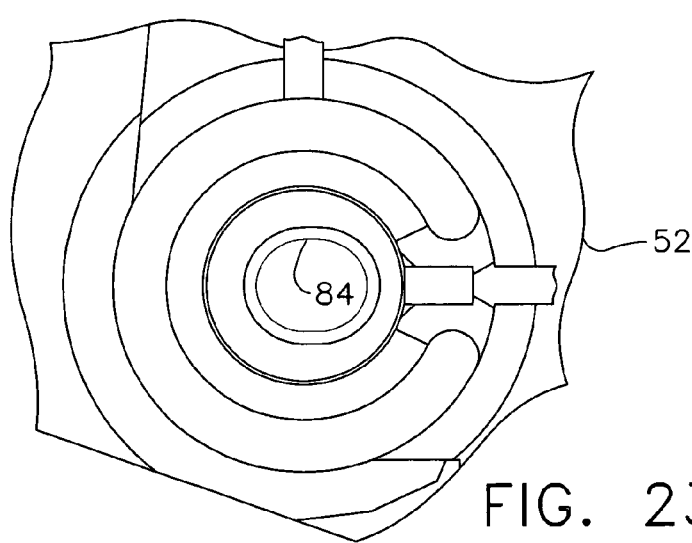
FIG. 23 is a left side detail view of the laterally elongate firing axle slot of the right handle housing shell of FIG. 22.
Figure 24:
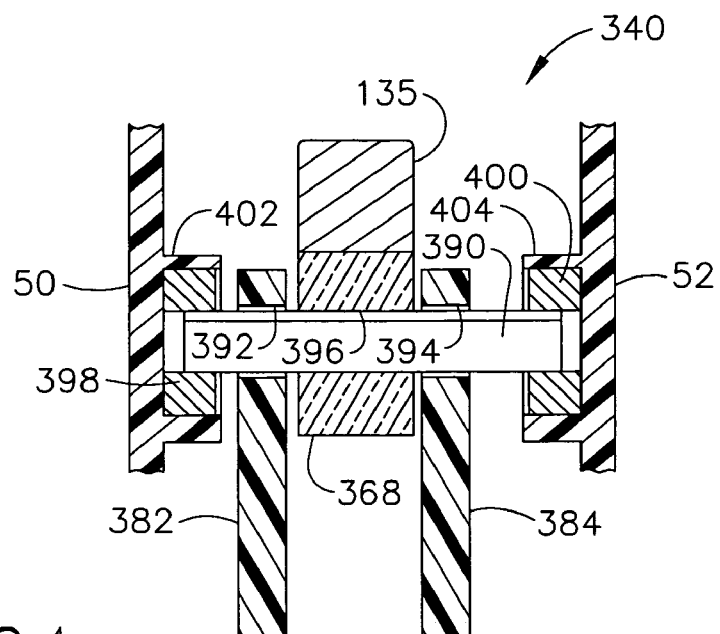
FIG. 24 is a diagrammatic aft view in vertical cross section of the small rack and brake assembly of the firing assistance mechanism of FIG. 4.

In FIGS. 16-19, interaction is depicted between the shuttle 300 of the assistance mechanism 19 and the rectangular plate 135 of the firing drive train 134. The cam finger 304 is generally an elongate rectangular plate with tapered in long sides presenting a front right corner that rotates clockwise, when viewed from above into a corresponding notch 322 about midway along a top left edge of the rectangular plate 135. Thus, the cam finger 304 may engage the rectangular plate 135 if inserted into the notch 322 with the shuttle 300 biased distally. In FIG. 16, tension spring firing assistance mechanism 19 of FIG. 4 in an initial, start state with the rectangular plate 135 retracted and with the plunger distally positioned and disengaged. An aft left surface of the cam finger 304 rests upon a kick-out cam step 324 attached to an internal surface of the left handle housing shell 50. It should be appreciated that a torsion coil spring and/or the lateral spacing around the cam finger 304 may bias the front, right surface of the cam finger 304 into contact with the rectangular plate 135 unless rotated counterclockwise, when viewed from above, by contact with the kick-out cam step 324. In FIG. 17, the tension spring firing assistance mechanism 19 of FIG. 16 has been armed by retracting the plunger 21 to an armed state (preload). The cam finger 304 is engaged into the notch 322 of the rectangular plate 135 and the tension spring 316 has been longitudinally stretched to store mechanical potential energy. In FIG. 18, the tension spring firing assistance mechanism 19 of FIG. 17 is being fired distally, the rectangular plate 135 being urged by the firing trigger 28 (not shown in FIGS. 16-19) and assisted by the spring-biased shuttle 300. The cam finger 304 has approached its most distal position as a beveled proximal surface of the kick-out cam step 324 contacts the aft left surface of the cam finger 304. In FIG. 19, tension spring firing assistance mechanism 19 of FIG. 18 has reached its unloaded, fired state with the cam finger 304 rotated counterclockwise as viewed from above out of engagement with the notch 322 in the rectangular plate 135, allowing a retraction bias and/or reverse movement of the firing trigger to retract the rectangular plate 135 (as shown in phantom).

In FIGS. 5 and 20-27, a selective engagement mechanism of the firing assistance mechanism 19 that couples a firing assistance force during firing includes both the selective engagement of the shuttle 300 to the rectangular plate 135 but also the selective release of the combination of the rectangular plate 135 and the shuttle 300 from a held proximal position relative to the handle portion 20. To that end, a small rack brake assembly 340 of the assistance mechanism 19 holds the rectangular plate 135, and thus the firing drive train 134, in a proximal position until firing commences. The firing trigger axle 83 passes through a distal end hole 342 of a horizontal brake link 344. A proximal abutment surface 346 of the horizontal brake link 344 is urged distally by a distally bowed leaf spring 348 having an upper looped end 350 engaged to a lateral pivot pin 352 extending from the left handle housing shell 50. A lower end 354 of the distally bowed leaf spring 348 is adjustably positioned longitudinally between the left and right handle housing shells 50, 52 by a cylindrical cam 356 having an off-center lateral through hole 358 that receives an adjustment axle 360 rotationally fixed by a pin 362 and turned by the adjustment knob 29. The cylindrical cam 356 is rightward biased from contact with the left handle housing shell 50 by a spring 363 (FIG. 5). A locking finger 364 passing transversely through the adjustment axle 360 frictionally engages at both ends a frictional ring surface 366 (FIG. 22) formed on an inner surface of the right handle housing shell 52 to hold the adjusted position. Adjustment allows the user to vary the amount of spring force distally biasing the firing trigger axle 83 via horizontal brake link 344.

A block-shaped brake pad 368 is moved into braking contact with a proximal undersurface of the rectangular plate 135 proximal to the proximal gear rack segment 136 when the horizontal brake link 344 is at its forward position with the firing trigger axle 83 at a distal end of the longitudinally elongate oval guides 84 laterally aligned in each handle housing shell 50, 52. The block-shaped brake pad 368 is moved out of braking contact with the proximal undersurface of the rectangular plate 135 when the horizontal brake link 344 is at its aft position with the firing trigger axle 83 moved away from the distal end of the longitudinally elongate oval guides 84. This aft movement occurs when the firing trigger 28 is depressed with some of the resistance reacted by the firing drive train 134 being transferred to the firing trigger axle 83 and ultimately into the distally bowed leaf spring 348.

Horizontal motion of the horizontal brake link 344 is converted to an aft and up rotational motion (when viewed from the left when engaging) at the brake pad 368 by an assembly that rotates as a plane laterally aligned by left and right lateral spacing pins 370, 372 that extend respectively into sliding contact with the left and right handle housing shells 50, 52. In particular, a lower rod-shaped axle 374 passes through a proximal lateral through hole 376 in the horizontal brake link 344 and through a lower horizontal through hole 378, 380 respectively in left and right upper brake arms 382, 384 that flank the horizontal brake link 344. The left and right lateral spacing pins 370, 372 extend respectively outward from the left and right upper brake arms 382, 384 from respective left and right holes 386, 388 above the respective lower horizontal through hole 378, 380. An upper square axle 390 passes through left and right upper through holes 392, 394 in the respective upper brake arms 382, 384 and a generally horizontally elongate rectangular through hole 396 (FIGS. 26-27) in the block-shaped brake 368. Left and right rectangular prism ends (shoe) 398, 400 with a lateral square cross section are attached to the ends of the upper square axle 390 on the lateral outside respectively of the left and right upper brake arms 382, 384. Each cubic end 398, 400 is received within a respective rectangular boss 402, 404 (FIGS. 21-22, 24-27) formed on the inner surface respectively of the left and right handle housing shells 50, 52.

Figure 25:
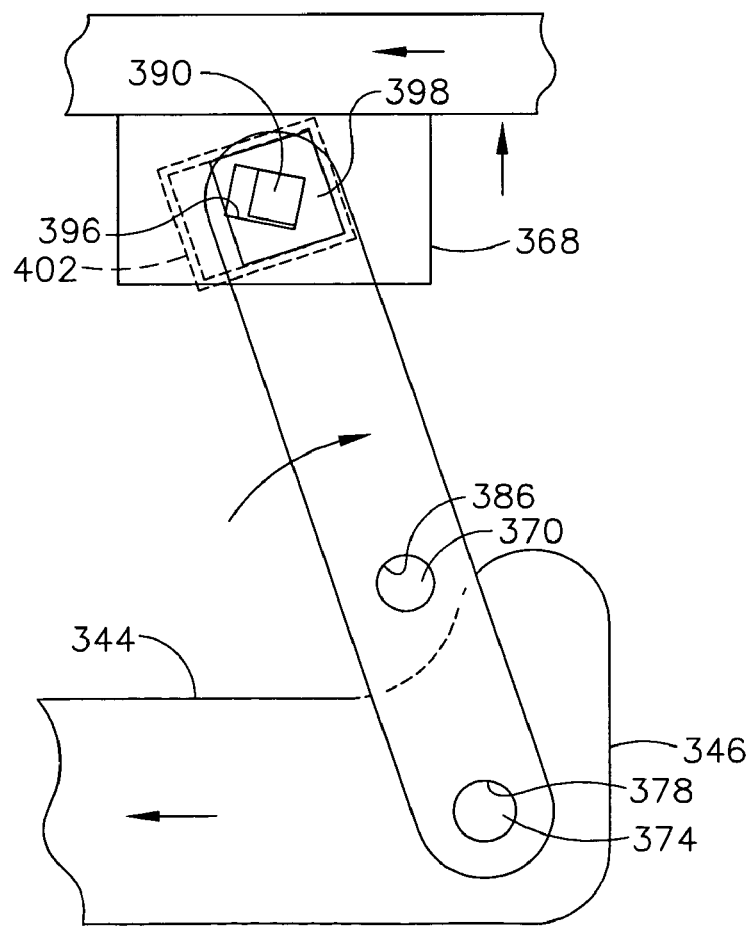
FIG. 25 is a left side detail view of a portion of the small rack, brake pad and brake linkages of the firing assistance mechanism of FIG. 4.
Figure 26:
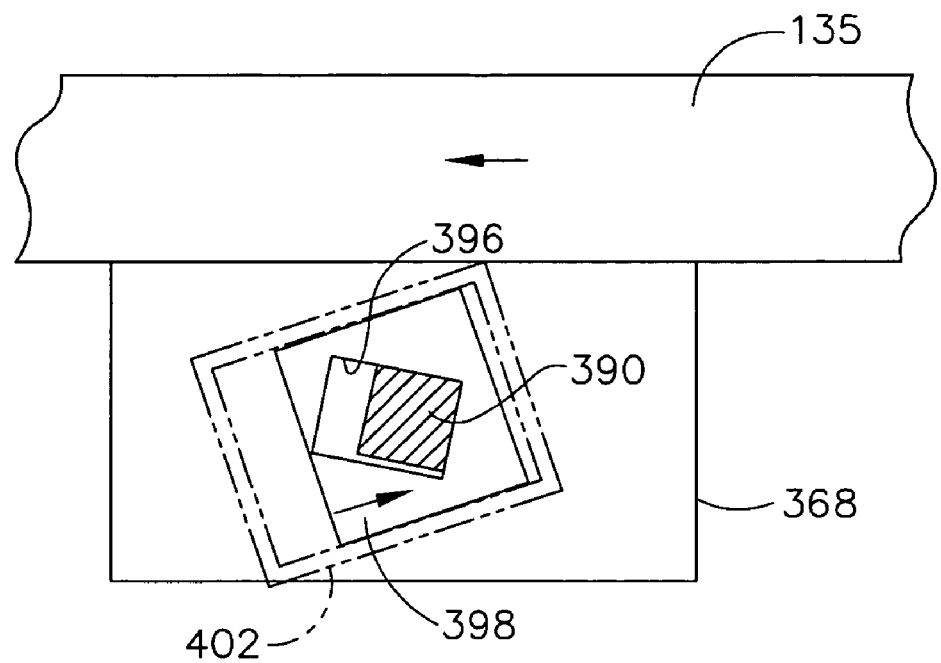
FIG. 26 is a left side detail view of the small rack and the small rack brake of FIG. 24 in a locked state.
Figure 27:
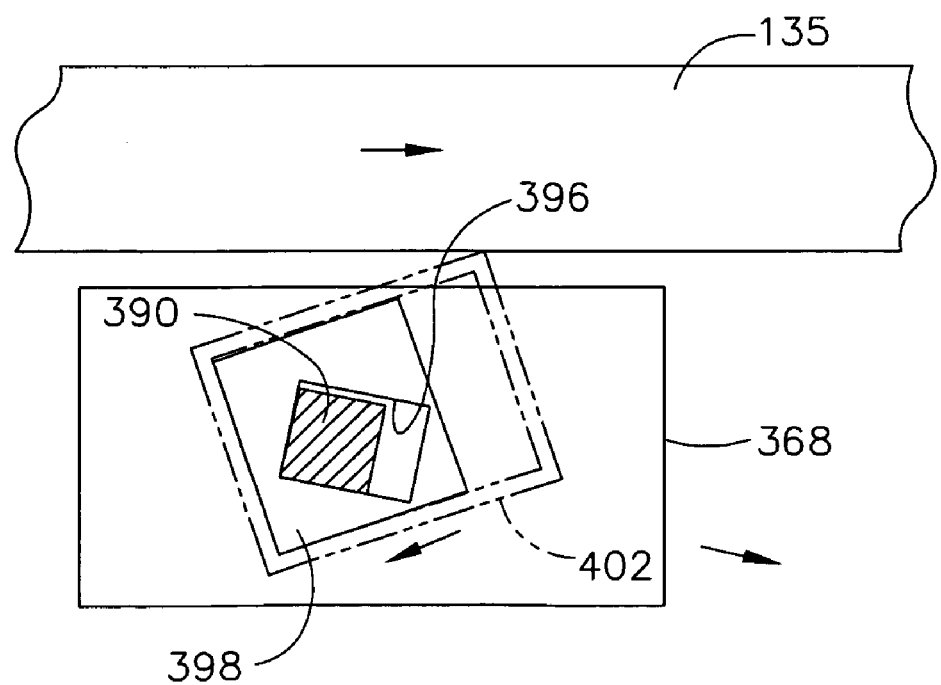
FIG. 27 is a left side detail view of the small rack and the small rack brake of FIG. 24 moved to an unlocked state.

It should be appreciated that the firing drive train 134 is generally held in a retracted position by the firing trigger return spring 124 rotating the firing trigger 28 clockwise, when viewed from the left. When the small rack brake assembly 340 is in its default, engaged position, as depicted in FIGS. 20-21, 25-26, with the horizontal brake link 344 forward and the upper brake arms 382, 384 top aft, the rectangular plate 135 is allowed to retract, as depicted as occurring in FIG. 19. However, the brake pad 368 creates sufficient frictional force to offset any tendency of the firing drive train 134 to be distally advanced solely under the influence of the assistance mechanism 19 that might otherwise overcome this retraction force. With particular reference to FIG. 25-26, the small rack brake assembly 340 is urged into the default, engaged position by the forward movement of the horizontal brake link 344. The left and right rectangular bosses 402, 404 are canted such that forward movement at the connection between the horizontal brake link 344 and upper brake arms 382, 384 causes the left and right shoes 398, 400 to move and aft and upward in the respective left and right bosses 402, 404. The upper square axle 390 can slide within the generally horizontal rectangular through hole 396 in the brake pad 368 to allow for retraction of the rectangular plate 135 and thus the firing drive train 134. In particular, the generally horizontal rectangular through hole 396 is slightly canted upward at its distal end. Thus frictional contact of the brake pad 368 to the under surface of the rectangular plate 135 during retraction slides the brake pad 368 proximally with the upper square axle 390 positioned in a slightly higher distal portion of the generally horizontal through hole 396, allowing a slight gap to occur between the surfaces (FIG. 27). Conversely, a distal bias on the firing drive train 134, such as when the assistance mechanism 19 is preload and engaged to the firing drive train 134, causes a slight distal movement of the brake pad 368, moving the upper square axle 390 to a slightly lower proximal portion of the generally horizontal through hole 396 in the brake pad 368, urging the brake pad 368 upwardly into braking contact with the rectangular plate 135.

Figure 28:
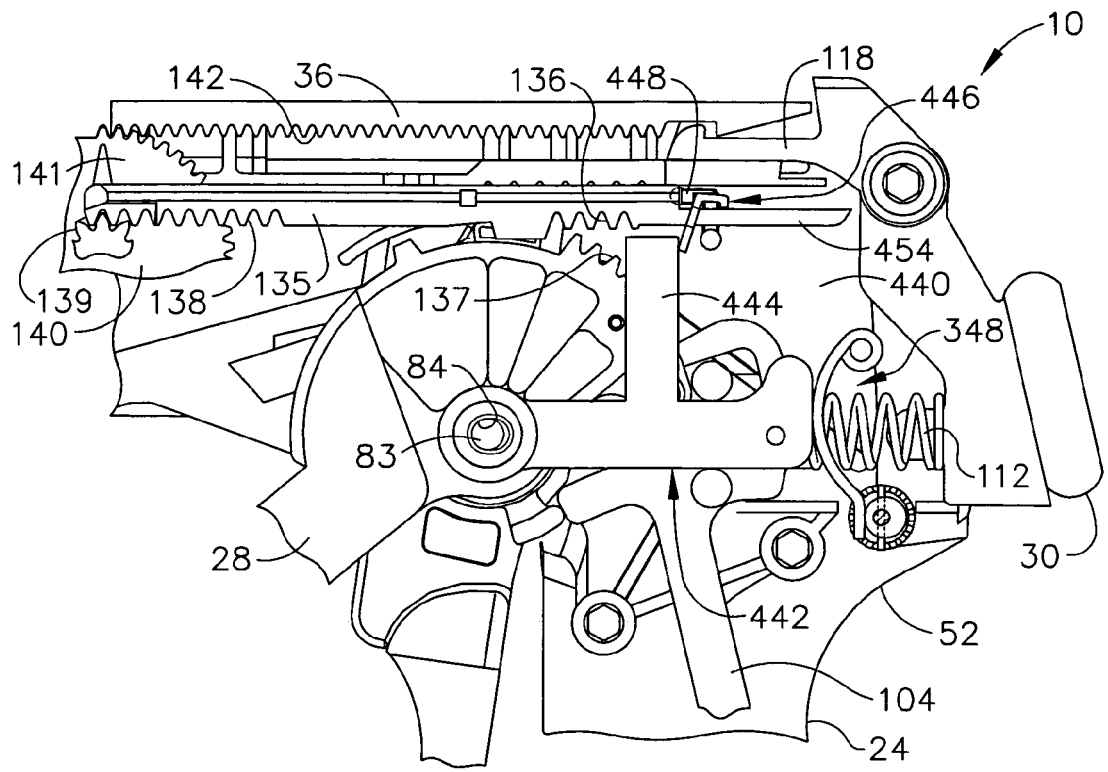
FIG. 28 is a left side view in elevation of a top aft portion of the handle with the left handle housing shell removed from the surgical stapling and severing instrument of FIG. 1 exposing a firing handle being fired to release an alternative small rack brake for the firing assistance mechanism of FIG. 4.
Figure 29:
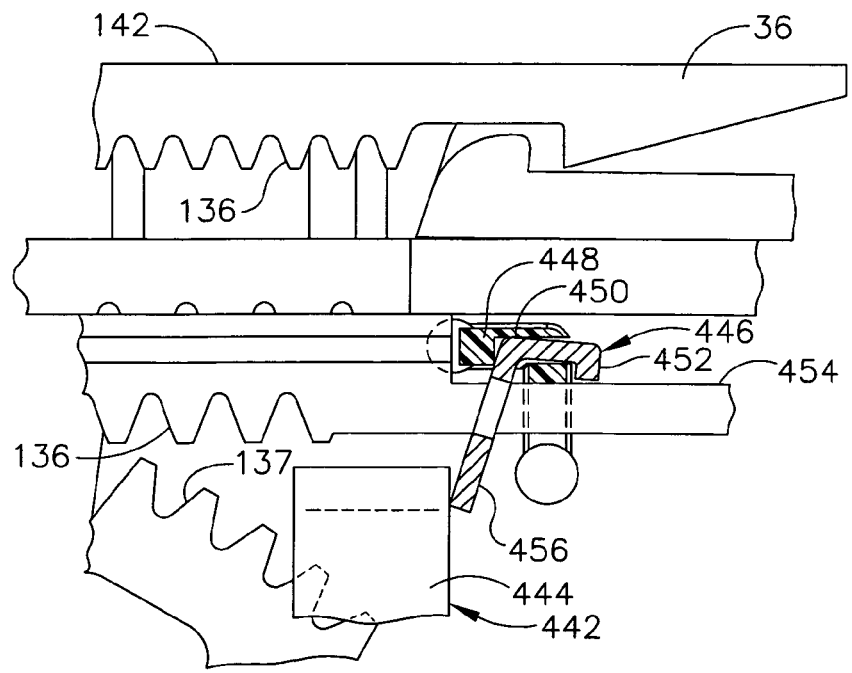
FIG. 29 is a left side detail view of the alternative small rack brake of FIG. 28.

In FIGS. 28-29, an alternate small rack braking assembly 440 includes the adjustable distally bowed leaf spring 348 that forward biases a horizontal brake link 442 and thus the firing trigger axle 83 as described above. An upper brake arm 444, however, is perpendicularly and rigidly attached at a midpoint of the horizontal brake link 442 to selectively rotate an inverted J-shaped brake arm 446. A resilient guide 448, formed in the left handle housing shell 52, positions a top portion 450 of the inverted J-shaped brake arm 446 so that a downwardly curved proximal end 452 is rotated downward into binding contact with a recessed top surface 454 formed in the proximal end of the rectangular plate 135. A distal downwardly hanging portion 456 of the inverted J-shaped brake arm 446 may be rotated proximally by a proximally moving upper brake arm 442 causing the downwardly curved proximal end 452 to lift off of the recessed top surface 454 allowing the firing drive train 134 to fire.

Figure 30:
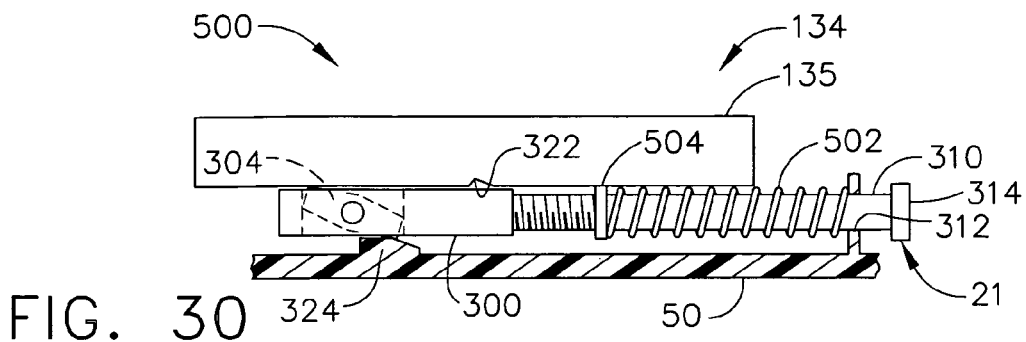
FIG. 30 is a top view of an alternative compression spring firing assistance mechanism in an initial, start state with a small rack retracted and an unloaded shuttle for the surgical stapling and severing instrument of FIG. 1.
Figure 31:
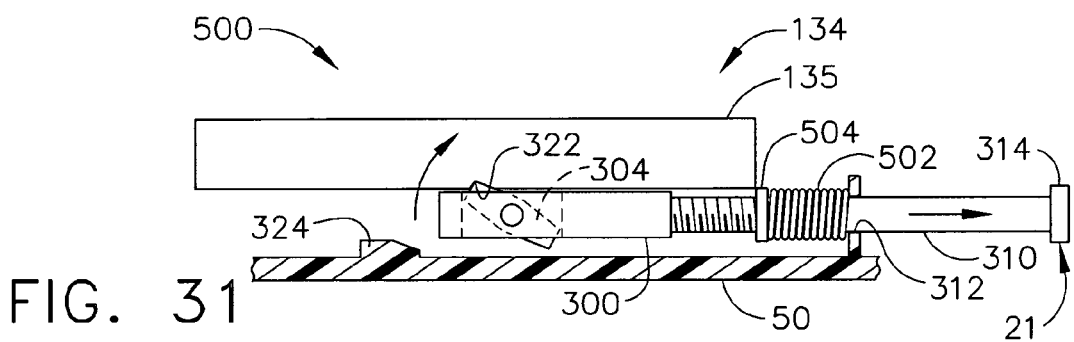
FIG. 31 is a top view of the compression spring firing assistance mechanism of FIG. 30 in an armed state (preload) with the small rack retracted and engaged to a retracted shuttle with a compressed compression spring.
Figure 32:
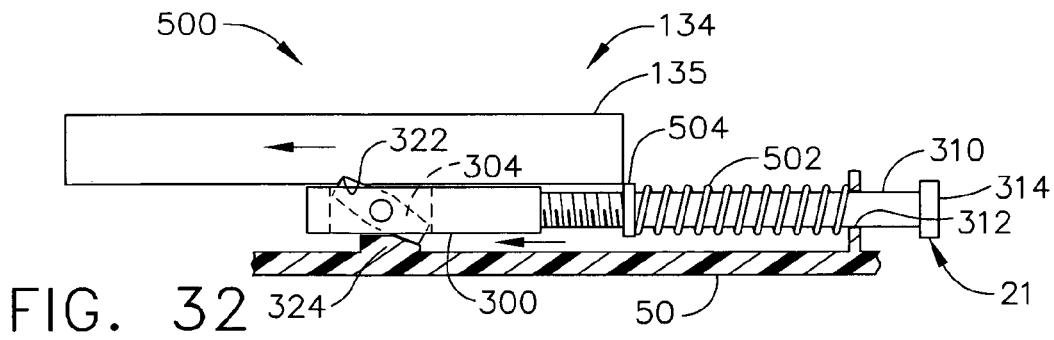
FIG. 32 is a top view of the tension spring firing assistance mechanism of FIG. 31 in a triggered state (firing) with the small rack being distally biased by the compression spring via the engaged shuttle while simultaneously being distally advanced by the firing trigger.
Figure 33:
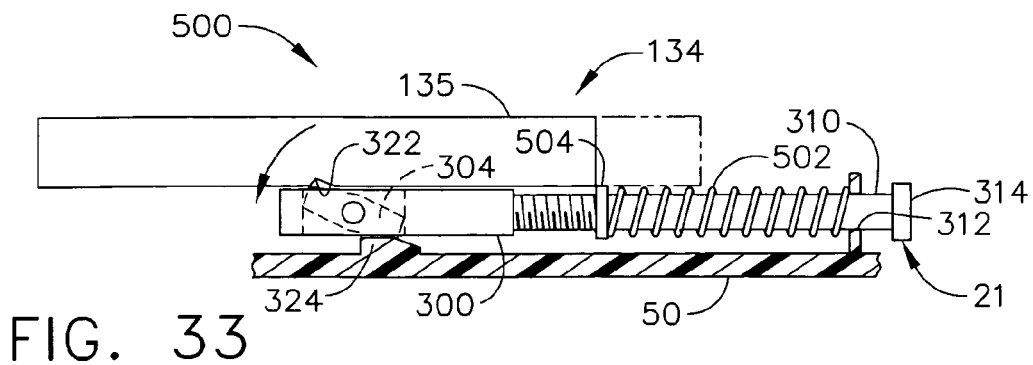
FIG. 33 is a top view of the tension spring firing assistance mechanism of FIG. 32 in a retraction state after firing with the small rack being proximally retracted (shown in phantom) to return to the initial state after disengagement from the distally-positioned plunger.
Figure 34:
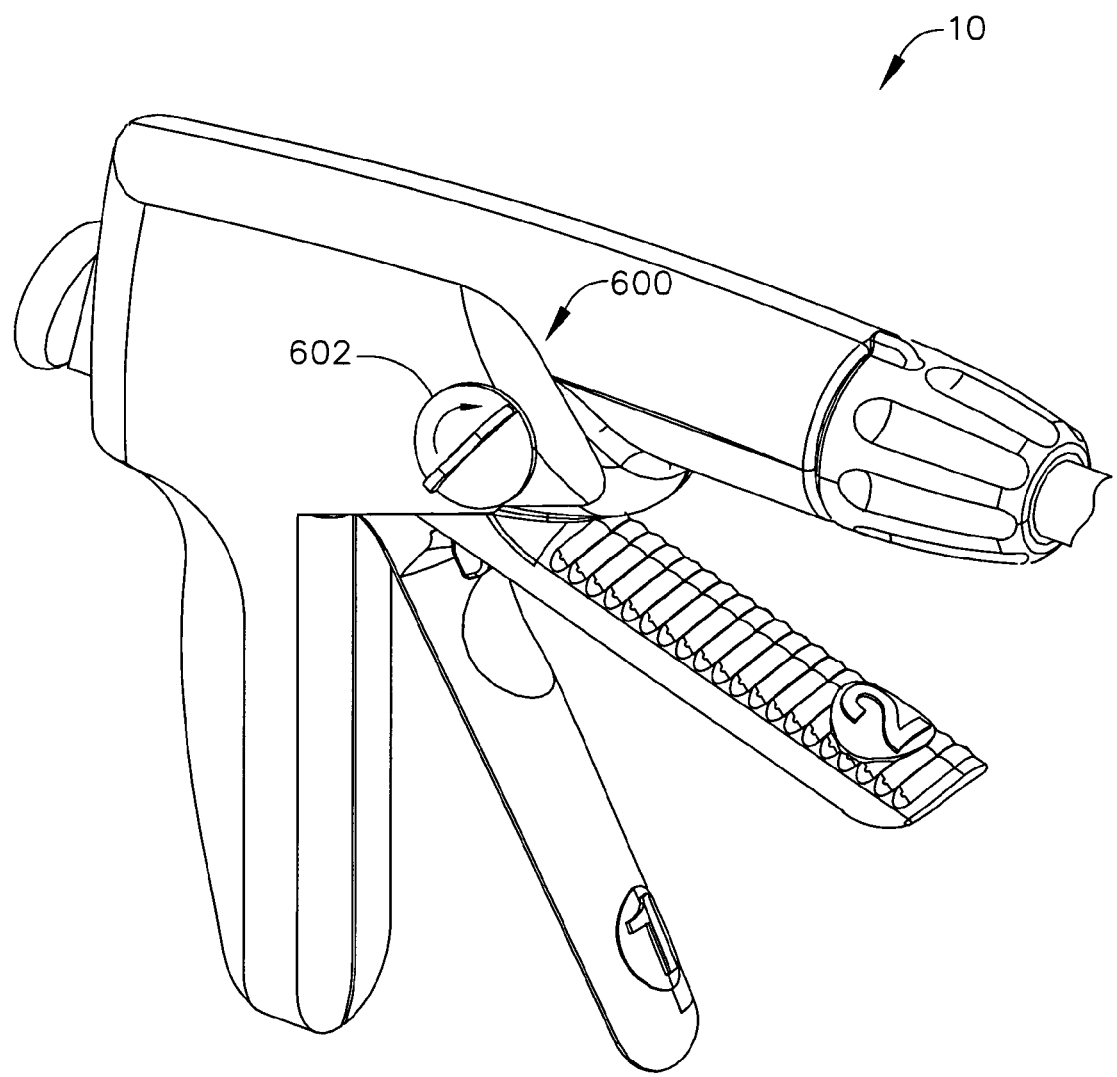
FIG. 34 is a front right perspective view of a handle of a surgical stapling and severing instrument with a wind-up firing assistance mechanism.
Figure 37:
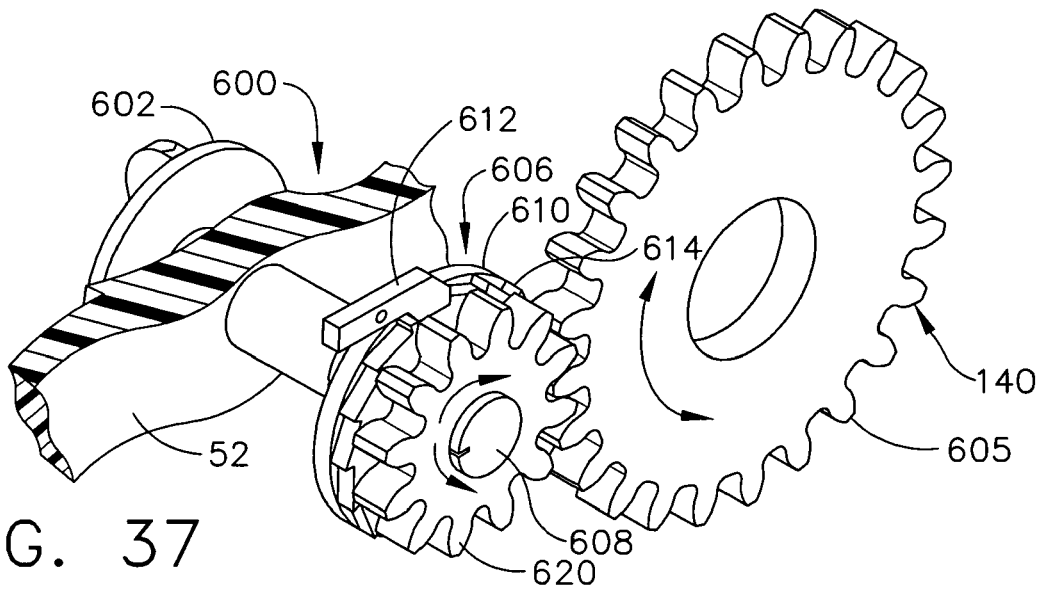
FIG. 37 is a front left isometric view of a winding knob, portion of housing, ratchet gear and an assisted spur gear of the wind up firing assistance mechanism of FIG. 34.
Figure 38:
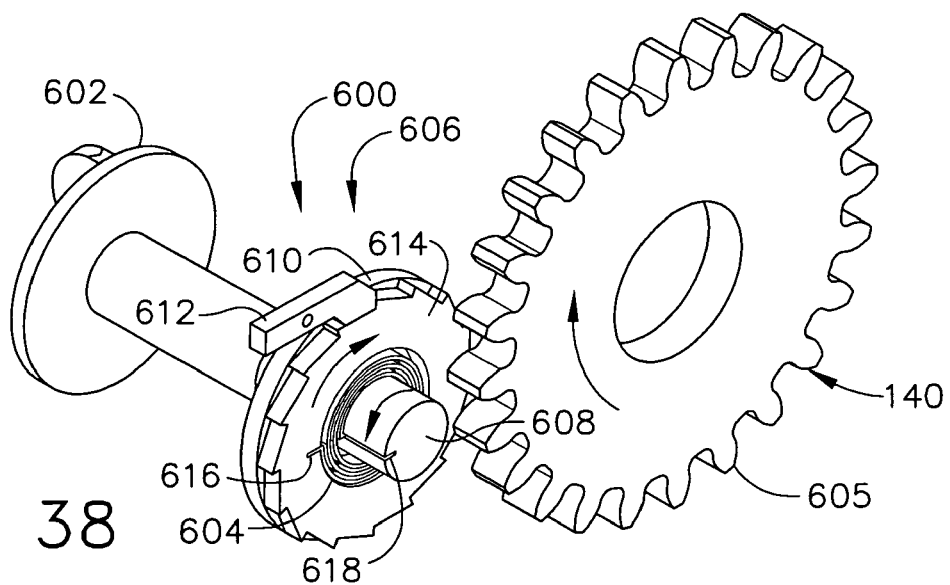
FIG. 38 is a front left isometric view of the winding knob, ratchet gear and an assisted spur gear multiplier gear of FIG. 37 with a small outer spur gear removed to expose a torsion coil spring of the ratchet gear.
Figure 39:
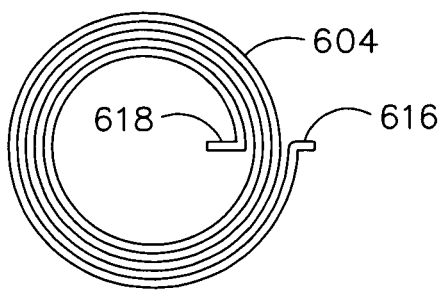
FIG. 39 is a side view of the torsion coil spring of FIG. 38 in a relaxed, loose coil.
Figure 40:
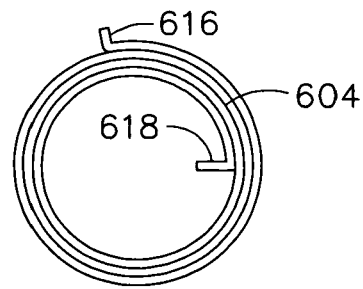
FIG. 40 is a side view of the torsion coil spring of FIG. 39 in an actuated, tight coil.

In FIGS. 30-33, an alternative firing assistance mechanism 500 includes the shuttle 300 that engages the rectangular plate 135 of the firing drive train 134 as previously described but urged with a compression spring 502 between a raised distal ring 504 formed on the cylindrical portion 310 of the plunger 21 and the plunger hole 312. In FIG. 30, the rectangular plate 135 and firing driving train 134 are retracted with the alternative firing assistance mechanism 500 in a distal, fired position with the compression spring 502 unloaded. In FIG. 31, the plunger 21 has been drawn aft, engaging the cam finger 304 and thus the shuttle 300 to the rectangular plate 135 as the compression spring 502 is compressed, storing mechanical potential energy. In FIG. 32, the assistance mechanism 500 has been triggered, the firing drive train 134 and shuttle 300 moving in unison as the cam finger 304 begins to contact the kick-out cam step 324. In FIG. 32, with further distal movement, the kick-out cam step 324 has rotated the cam finger 304 counterclockwise as viewed from above out of engagement with the notch 322 in the rectangular plate 135, which would be followed by retraction of the firing drive train 134. The alternative firing assistance mechanism 500 may utilize either brake assembly 340, 440.

In FIGS. 34-40, another alternative wind-up firing assistance mechanism 600 incorporated into the surgical stapling and severing instrument 10 includes a wind-up knob 602 that stores mechanical potential energy in a torsion coil spring 604 in a ratchet gear 606 that is in gear engagement to a third spur gear 605 coaxially attached to the right side of the coaxial dual spur gear (multiplier gear) 140 (FIGS. 35, 36). A shaft 608 connects to the wind-up knob 602, passes through the right handle housing shell 52 and is attached to a circular flange 610 that pivotally holds a downwardly biased ratchet pawl 612 that engages a rotatingly received ratchet gear 614 with teeth angled such that counterclockwise rotation of the ratchet gear 614, when viewed from the right, is prevented the torsion coil spring 604 has an outer end 616 that is engaged to the ratchet gear 614 and an inner end 618 that is engaged to the shaft 608. A spur gear 620 is attached for rotation with the ratchet gear 614 and is in gear engagement with the third spur gear 605 added to the coaxial dual spur gear (multiplier gear) 140. The third spur gear 605 that is coaxially attached to the right side of the dual spur gear 140 that is in gear engagement with the spur gear 620 of the ratchet gear 606 may be sized to provide a desired gear ratio between the assistance mechanism 500 and the firing drive train 134. The alternative firing assistance mechanism 600 may utilize either brake assembly 340, 440.

In FIGS. 41-52, in addition to or as an alternative of direct assistance in moving a firing drive train 134 in a surgical stapling and severing instrument 10, firing assistance may be incorporated by disengaging a retraction force on the firing drive train 134 during firing. Thereby, the surgeon is not required to exert as great a force on the firing trigger 28 yet retains the advantages of automatic retraction of the firing drive train 134 after firing. To that end, an assistance mechanism 700 is incorporated into the surgical stapling and severing instrument 10 with a shuttle 702 that is proximate to a left side and aligned for movement with the rectangular plate 135 having a reversed notch 704 near a distal end along a top left surface thereof. Rather than being connected directly to the firing trigger 28, a retraction tension spring 706 whose fixed end (not shown) is attached in the pistol grip 24 has a moving end 708 that is connected to a cable 710 that turns on a pulley 712 and is attached to a proximal end of the shuttle 702. The pulley 712 is aligned to the longitudinal travel of the shuttle 702 and is more proximal than a most proximal position of the shuttle 702.

Figure 51:
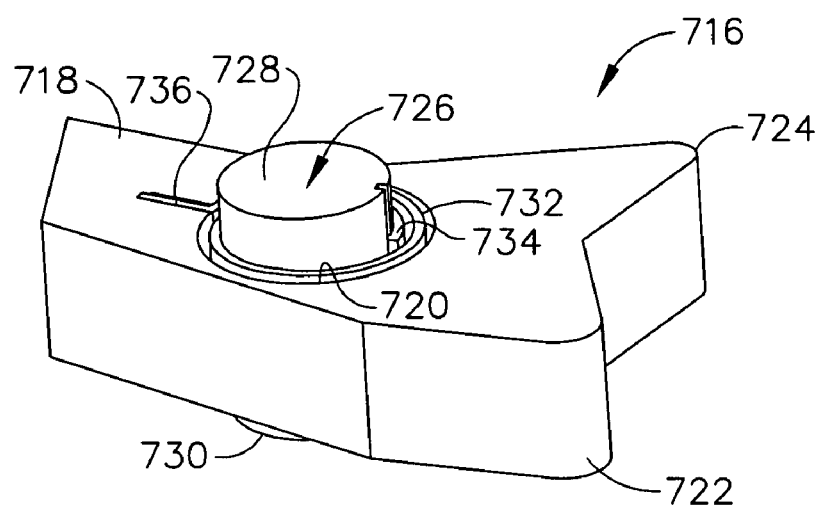
FIG. 51 is an isometric view of the dual locking cam assembly of FIG. 43.
Figure 52:
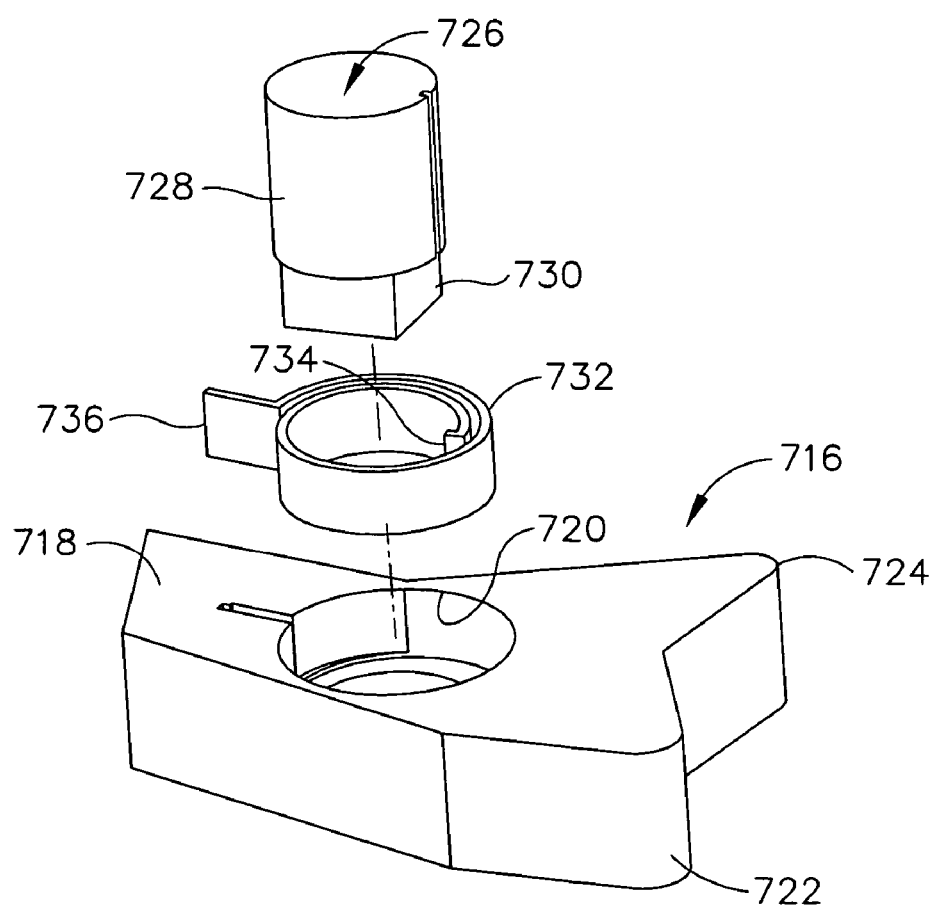
FIG. 52 is an isometric disassembled view of the dual locking cam assembly of FIG. 44.

A lateral through slot 714 near a distal end of the shuttle 702 receives a horizontally rotating dual engagement cam member 716 that selectively engages the left handle housing shell 50 or the firing drive train 134. With particular reference to FIGS. 51-52, the dual engagement cam member 716 has a leftward canted distal end 718 that is distal to a vertical pivot through hole 720 and left and right proximal fingers 722, 724 that are proximal to the vertical pivot through hole 720. A cam axle 726 has a cylindrical upper portion 728 that allows rotation of the cam member 716 with a square lower portion 730 that is fixedly received into the shuttle 702 below the lateral through slot 714. A torsion coil spring 732 has an inner end 734 attached to the cylindrical upper portion 728, is wrapped counterclockwise as viewed from above, and has an outer end 736 engaged to the cam member 716 such that the cam member 736 is biased clockwise into contact with the rectangular plate 135 of the firing drive train 134.

Figure 41:
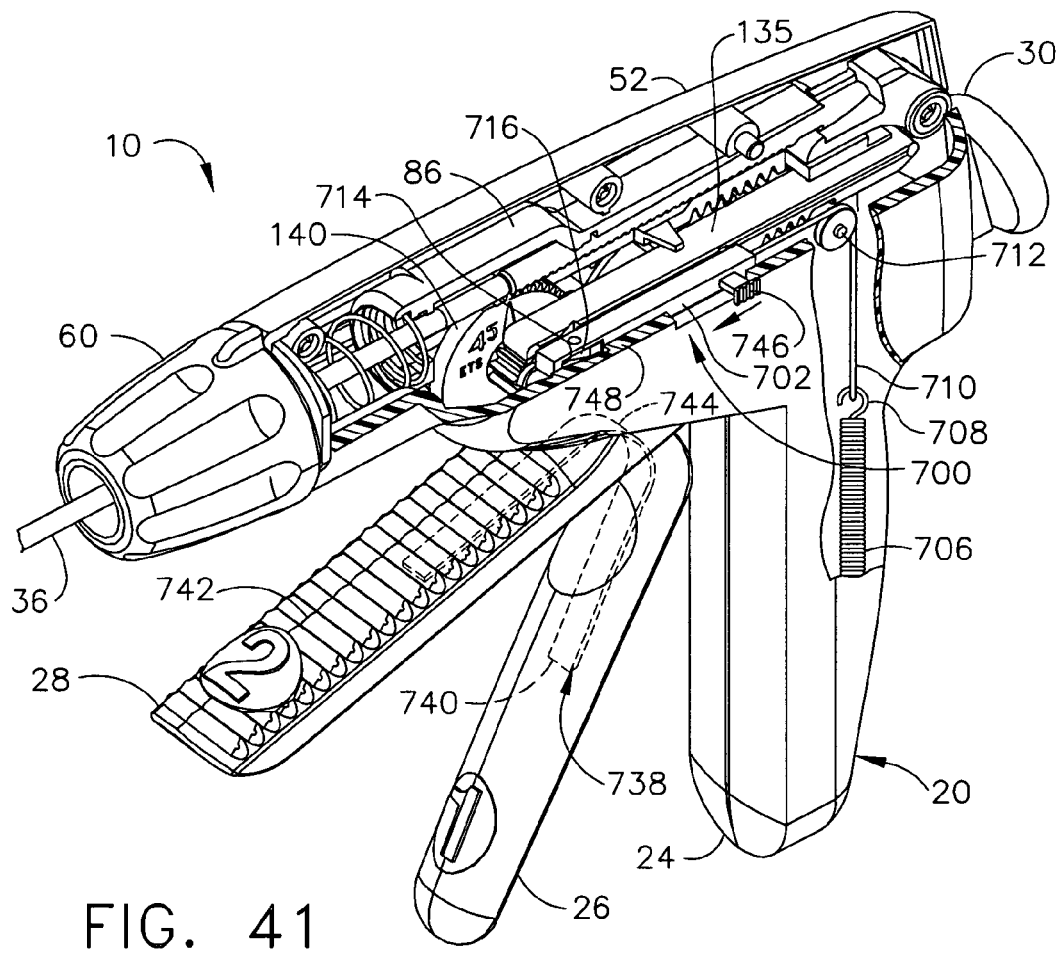
FIG. 41 is a front left perspective view of a handle of a surgical stapling and severing instrument including a retraction disengagement firing assistance mechanism.

With particular reference to FIG. 41, a bent leaf spring 738 (shown in phantom) has a first end 740 inserted into the closure trigger 26 and a second end 742 inserted into the firing trigger 28 with a curved portion 744 there between biased to separate the two triggers 26, 28. The bent leaf spring 738 compensates to a lesser degree for the disengagement of the retraction tension spring 706 from the firing trigger 28 by keeping the firing trigger 28 from sagging and interfering with use of the closure trigger 26.

Figure 42:
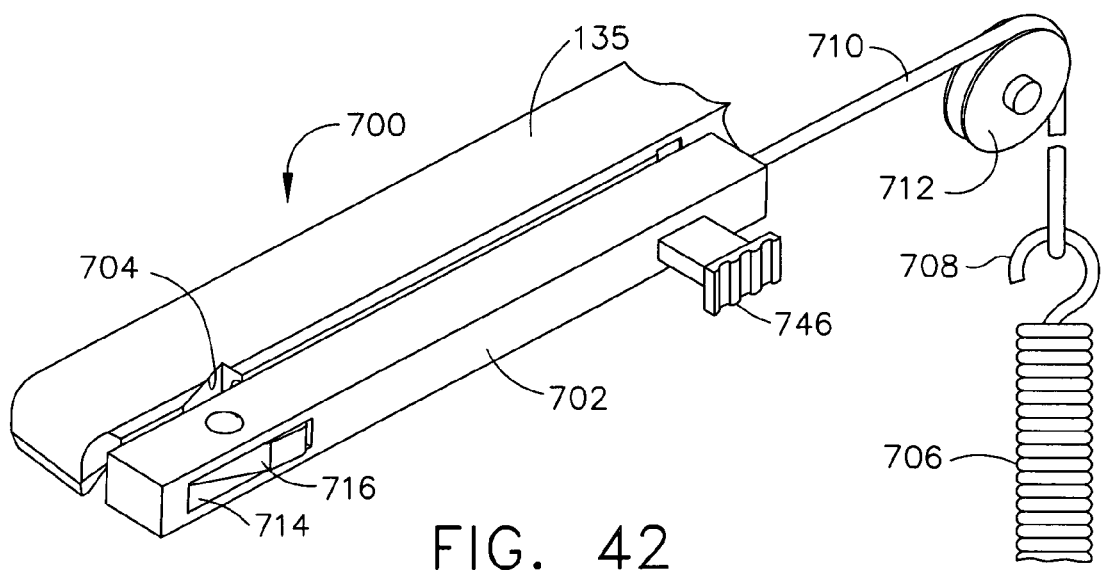
FIG. 42 is a front left isometric detail view of a small rack and shuttle of the retraction disengagement firing assistance mechanism of FIG. 41.

In FIGS. 41-42, the assistance mechanism 700 is preload in preparation for use of the surgical stapling and severing instrument 10 by distally sliding a retraction assistance slide grip 746 that rides longitudinally along an actuator horizontal slot 748 (FIG. 41) formed in the left handle housing shell 50.

Figure 43:
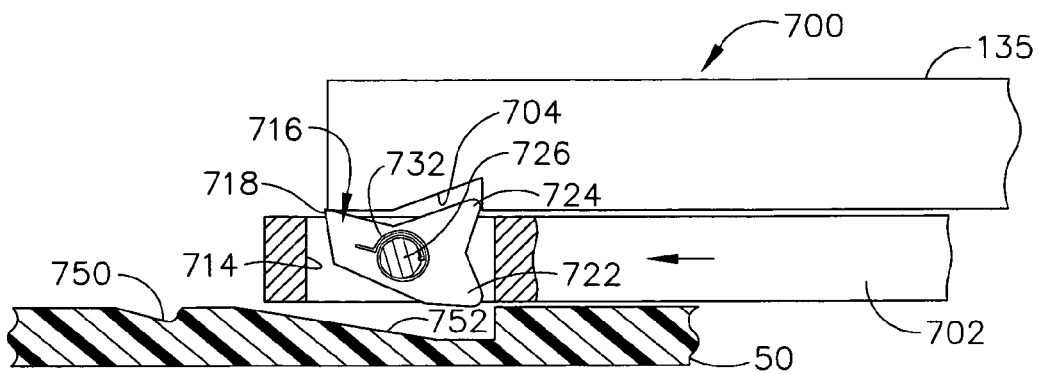
FIG. 43 is a top view of the retraction disengagement firing assistance mechanism of FIG. 41 in an initial state, start state with a small rack and shuttle retracted.
Figure 44:
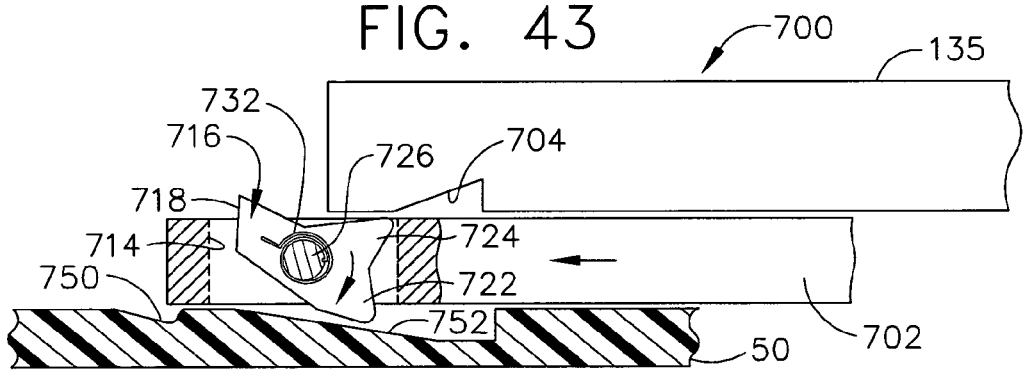
FIG. 44 is a top view of the retraction disengagement firing assistance mechanism of FIG. 43 being armed by distally advancing the shuttle with the small rack remaining retracted.
Figure 45:
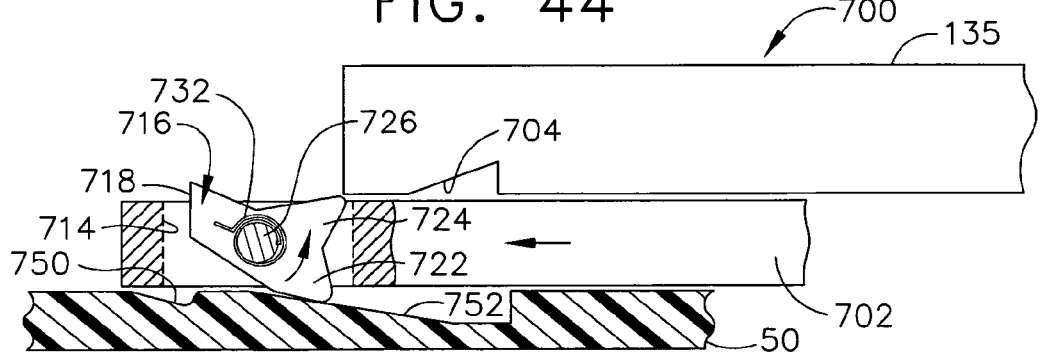
FIG. 45 is a top view of the retraction disengagement firing assistance mechanism of FIG. 44 being armed by further distally advancing the shuttle with the small rack remaining retracted.
Figure 46:
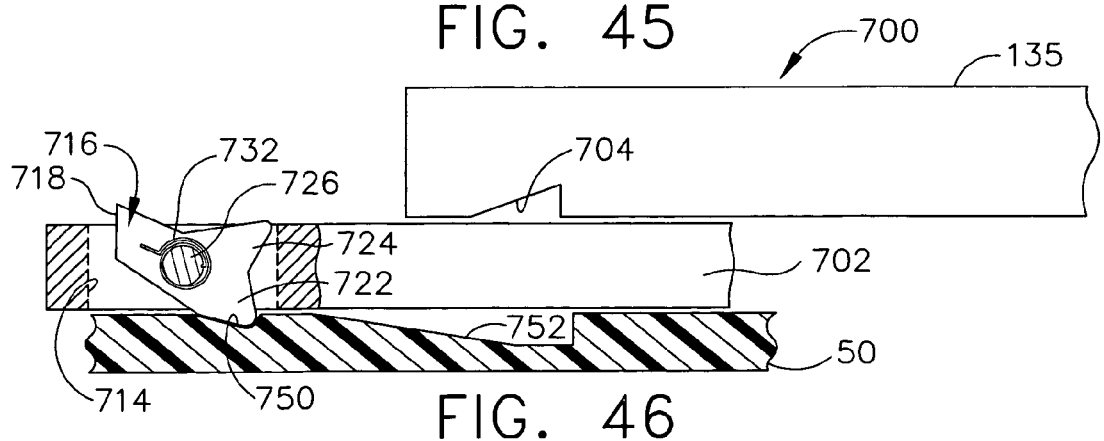
FIG. 46 is a top view of the retraction disengagement firing assistance mechanism of FIG. 45 armed (pre-loaded) by a dual locking cam assembly being pivoted within the shuttle into engagement with the handle housing while the small rack remains retracted.
Figure 47:
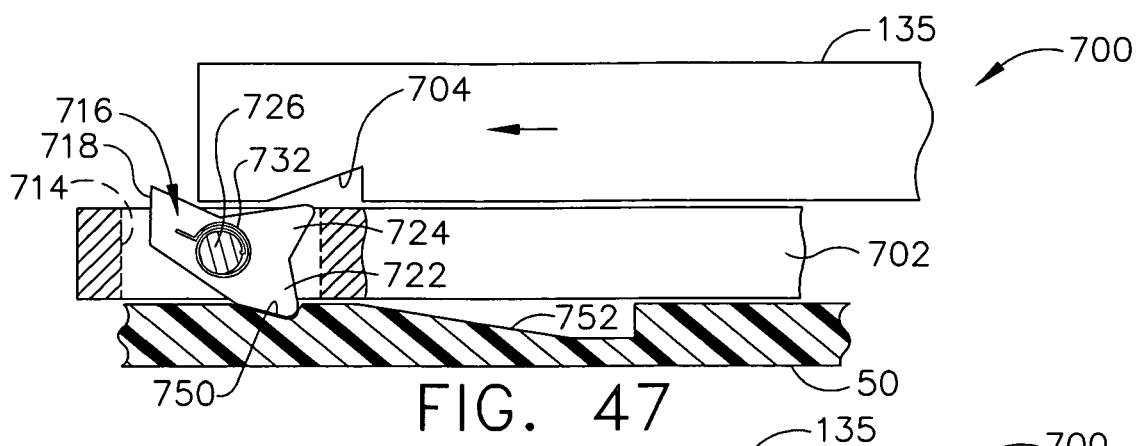
FIG. 47 is a top view of the retraction disengagement firing assistance mechanism of FIG. 46 remaining armed (pre-loaded) as the small rack distally advances during firing of the surgical stapling and severing instrument.
Figure 48:
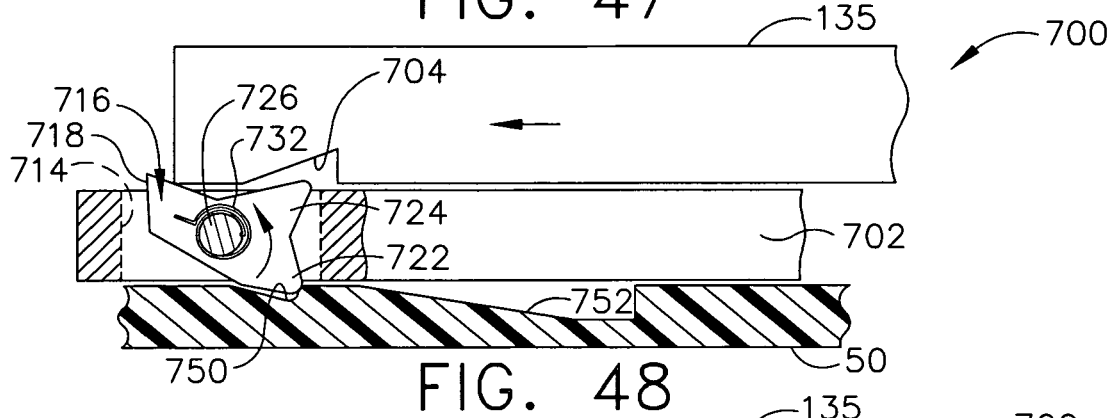
FIG. 48 is a top view of the retraction disengagement firing assistance mechanism of FIG. 47 with the small rack distally advanced to approximately full travel into contact with the dual locking cam assembly to effect disengagement from the handle housing.
Figure 49:
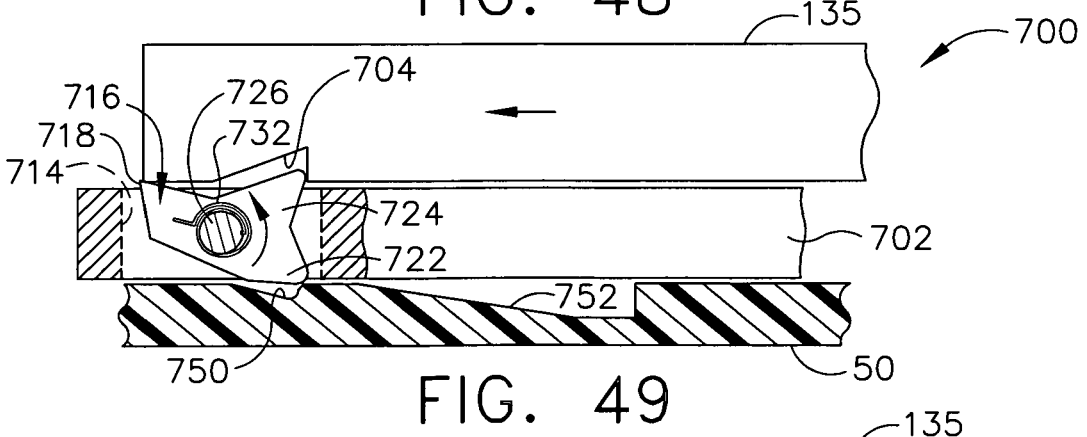
FIG. 49 is a top view of the retraction disengagement firing assistance mechanism of FIG. 48 with the small rack fully distally advanced to rotate the dual locking cam assembly fully out of engagement with the handle housing and into engagement with the small rack.
Figure 50:
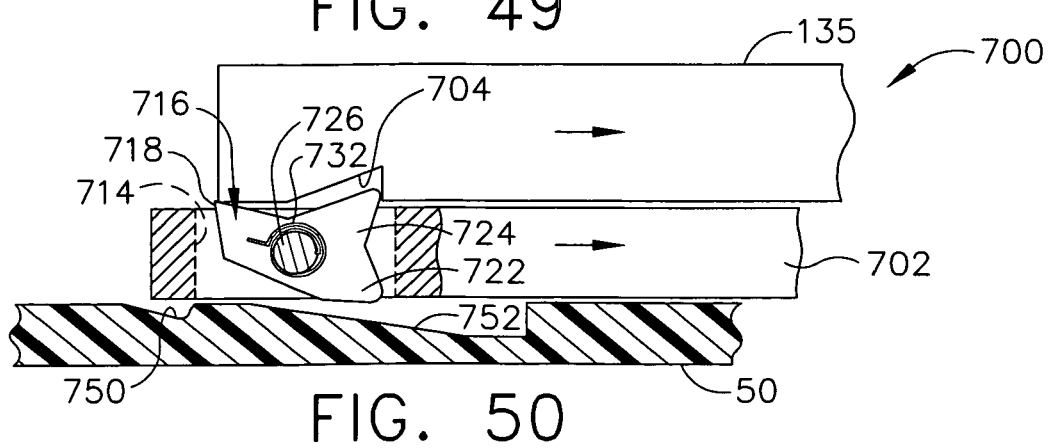
FIG. 50 is a top view of the retraction disengagement firing assistance mechanism of FIG. 49 with the small rack retracting under the retraction bias from the shuttle.

In FIGS. 43-50, a small, distal ramped notch 750 and a large, proximal ramped notch 752 formed on an inner surface of the left handle housing shell 50 in combination with the aligned cam member 716 act as an engagement mechanism that selectively engage the shuttle 702 to the left handle housing shell 50, the rectangular plate 135 of the firing drive train 134, or to neither. In FIG. 43, the rectangular plate 135, and thus the firing drive train 134, are in a retracted, unfired position. The shuttle 702 is also retracted in an initial unloaded state. The cam member 716 is positioned to the right of the large, proximal ramped notch 752. The clockwise bias of the torsion coil spring 732 on the cam member 716 tends to rotate the left proximal finger 722 into the large, proximal ramped notch 752 and the right proximal finger 724 out of the reversed notch 704 in the rectangular plate 135 to the extent allowed by the leftward canted distal end 718 as the shuttle 702 is distally advanced in FIG. 44, preloading the retraction tension spring 706 (FIG. 41). In FIG. 45, the cam member 716 rotates counterclockwise as the left proximal finger 722 exits the large, proximal ramped notch 752 in preparation for engaging the right handle housing shell 50, which occurs as the shuttle 702 reaches full distal travel in FIG. 46. The shallow nature of the small, distal ramped notch 750 allows sufficient clockwise rotation of the cam member 716 such that the left proximal finger 722 is in the small, distal ramped notch 750, the right proximal finger 724 is approximately flush with a right edge of the shuttle 702, and the leftward canted distal end 718 of the cam member 716 extends slightly into the space traversed by the rectangular plate 135 of the firing drive train 134. In FIG. 47, the rectangular plate 135 of the firing drive train 134 is distally advancing as the firing trigger 28 (FIG. 41) is depressed during firing. A distal left corner of the rectangular plate 135 is approaching the leftward canted distal end 718 of the cam member 716 as the reversed notch 704 moves along the right side of the right proximal finger 724 of the cam member 716. In FIG. 48, the rectangular plate 135, contacting the leftward canted distal end 718 of the cam member 716, progressively rotates the cam member 716 counterclockwise, thus drawing the left cam finger 722 of the cam member 716 out of engagement with the small, distal ramped notch 750 in the left handle housing shell 50 and positions the right proximal finger 724 into the reversed notch 704 of the rectangular plate 135. In FIG. 49, further distal advancement to nearly full firing travel of the rectangular plate 135 has disengaged the cam member 716 from the right handle housing shell 50 and engaged the cam member 716 to the rectangular plate 135 of the firing drive train 134, thus coupling the extended retraction tension spring 706 (FIG. 41) to create a retraction bias. In FIG. 50, as the firing trigger 28 (FIG. 41) is released, the retraction bias retracts the shuttle 702 and thus the rectangular plate 135 (via the engaged cam member 716) back toward the initial state of FIG. 43.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, an assistance mechanism consistent with aspects of the invention may be coupled in other ways to the firing rod rather than interposing a multiplier gear between a primary rack that is attached to the firing rod and a small secondary rack.

As another example, a retraction assistance mechanism, consistent with aspects of the invention, may store biasing energy in a compression spring or torsion coil spring or other resilient member (e.g., charged gas cylinder) rather than a tension spring, similar to the versions that biased the firing assistance mechanism.

As yet another example, while a surgical stapling and severing instrument benefits from pre-loaded assistance in firing and/or retraction, other surgical instruments may benefit from aspects consistent with the present invention, to include but are not limited to a linear stapler, a circular stapler, an anastomosis instrument, etc.

As yet an additional example, a surgical stapling and severing instrument may benefit from incorporating a dual firing and retraction assistance mechanism that includes preloading for both assistance during the firing stroke and during the retraction of a firing drive train.

As yet a further example, while a single firing stroke has been described for clarity, a multiple firing stroke surgical instrument, such as described in the above-referenced U.S. patent application Ser. No. 11/052,632, may benefit from aspects consistent with the present invention.

What is claimed is:

1. A surgical instrument, comprising:
   a handle;
   an elongate implement portion extending distally from said handle and further comprising at least one deformable fastener member adjacent to a distal end of the elongate implement portion;
   a firing mechanism for deforming the at least one deformable fastener member to securely attach the at least one deformable fastener member to tissue, comprising:
      a distal portion received for longitudinal reciprocating motion in the elongate implement portion, and
      a proximal portion received in the handle for reciprocating movement between an unfired position and a fired position and coupled to the distal portion to transfer the related longitudinal reciprocating motion;
   a firing actuator movably attached to the handle and coupled to move the proximal portion of the firing mechanism from the unfired position to the fired position to attach the at least one deformable fastener member to tissue; and
   an assistance mechanism, comprising:
      a follower member received in the handle, proximate and aligned for movement between the unfired and fired positions of the proximal portion of the firing mechanism,
      a biasing member operatively configured to urge the follower member in a selected direction between unfired and fired positions and to be preloaded by movement of the follower member in an opposing direction, and
      an engagement mechanism operatively configured, in response to the proximal portion of the firing mechanism beginning movement in the selected direction, to engage the preloaded follower member to the proximal portion of the firing mechanism, wherein the preload assistance mechanism urges the firing mechanism in the selected direction during reciprocation of the firing mechanism to deformably attach the at least one deformable fastener to tissue.

2. The surgical instrument of claim 1, wherein the follower member comprises a linearly moving shuttle, the biasing member comprising a linear spring attached between the handle and the linearly moving shuttle.

3. The surgical instrument of claim 2, wherein the linear spring comprises a tension spring.

4. The surgical instrument of claim 2, wherein the linear spring comprises a compression spring.

5. The surgical instrument of claim 1, wherein the proximal portion of the firing mechanism comprises a rack, the follower member comprises a gear train, and the biasing member comprises a torsion coil spring biased ratchet gear attached to the handle.

6. The surgical instrument of claim 1, wherein the selected direction for assistance is firing from the unfired position to the fired position, the engagement mechanism further comprising a brake coupled to the proximal portion of the firing mechanism and responsive to actuation of the firing actuator to release.

7. The surgical instrument of claim 6, wherein the brake comprises a leveraged brake pad having a pivot point moved relative to the handle in response to actuation of the firing actuator to move the leveraged brake pad out of coupled engagement with the proximal portion of the firing mechanism.

8. The surgical instrument of claim 6, wherein the brake comprises a brake arm having a rotated portion positioned to rotate into coupled engagement with the proximal portion of the firing mechanism in response to actuation of the firing actuator.

9. The surgical instrument of claim 6, wherein the follower member comprises a shuttle, the engagement mechanism further comprising a locking cam biased into engagement with the proximal portion of the firing mechanism, and the handle comprising a disengaging cam positioned to move the locking cam out of engagement with the proximal portion of the firing mechanism as the shuttle approaches the fired position.

10. The surgical instrument of claim 6, further comprising a spring attached between the handle and the proximal portion of the firing mechanism to impart a retraction bias.

11. The surgical instrument of claim 10, wherein the spring comprises a tension spring having an attachment point to the handle proximal to an attachment point to the proximal portion of the firing mechanism.

12. The surgical instrument of claim 1, wherein the selected direction is retraction from the fired position to the unfired position, the follower member comprises a shuttle, the engagement mechanism further comprises a locking cam responsive to movement of the shuttle to the fired position to engage the handle resisting corresponding preloading of the biasing member and responsive to movement of the proximal portion of the firing mechanism approaching the fired position to disengage from the handle and to engage the proximal portion of the firing mechanism.

13. The surgical instrument of claim 12, wherein the biasing member comprises a tension spring attached to the handle proximal to an attachment to the shuttle.

14. A surgical instrument, comprising:
a handle;
an elongate implement portion extending distally from the handle and further comprising at least one deformable fastener member adjacent to a distal end of the elongate implement portion;
a firing drive train, comprising:
a distal portion received for longitudinal reciprocating motion in the elongate implement portion, the reciprocating motion of the distal portion deforming the at least one deformable fastener to attach the fastener to tissue, and
a proximal portion received in the handle for reciprocating movement between an unfired position and a fired position and coupled to the distal portion to transfer the related longitudinal reciprocating motion;
a firing trigger pivotally attached to the handle and coupled to move the proximal portion of the firing drive train from the unfired position to the fired position to attach the at least one deformable fastener to tissue; to tissue and
a firing assistance mechanism, comprising:
a follower member received in the handle, proximate and aligned for movement between the unfired and fired positions of the proximal portion of the firing drive train,
a biasing member operatively configured to become preload by movement of the follower member from the fired position to the unfired position,
an engagement mechanism operatively configured to engage the follower member to the proximal portion of the firing drive train in response to the follower member being retracted to the unfired position and to disengaging the follower member from the proximal portion of the firing drive train in response to the engaged follower member and firing drive train being fired to the fired position, wherein the engaged firing assistance mechanism transfers the preload from the biasing member to the firing mechanism during the firing stroke to deformably attach the at least one deformable fastener to tissue, and
a brake operatively configured to maintain the proximal portion of the firing drive train retracted until the firing trigger is actuated for firing.

15. The surgical instrument of claim 14, wherein the follower member comprises a linearly moving shuttle, the biasing member comprising a linear spring attached between the handle and the linearly moving shuttle.

16. The surgical instrument of claim 15, wherein the linear spring comprises a tension spring, the linearly moving shuttle further comprising a control externally exposed on the handle.

17. The surgical instrument of claim 15, wherein the linear spring comprises a compression spring, the linearly moving shuttle further comprising a control externally exposed on the handle.

18. The surgical instrument of claim 14, wherein the proximal portion of the firing drive train comprises a rack, the follower member comprises a gear train, and the biasing member comprises a torsion coil spring biased ratchet gear attached to a rotation knob externally exposed on the handle.

19. The surgical instrument of claim 14, wherein the brake comprises a leveraged brake pad having a pivot point moved relative to the handle in response to a forward biased axle of the firing trigger moving aft in response to actuation of the firing trigger, moving the leveraged brake pad out of coupled engagement with the proximal portion of the firing drive train.

20. The surgical instrument of claim 14, wherein the brake comprises a brake arm having a rotated portion positioned to rotate into coupled engagement with the proximal portion of the firing drive train in response to a forward biased axle of the firing trigger moving aft in response to actuation of the firing actuator.

21. The surgical instrument of claim 14, wherein the follower member comprises a shuttle, the engagement mechanism further comprising a locking cam biased into engagement with the proximal portion of the firing drive train, and the handle comprising a disengaging cam positioned to move the locking cam out of engagement with the proximal portion of the firing drive train as the shuttle approaches the fired position.

22. The surgical instrument of claim 14, further comprising a spring attached between the handle and the proximal portion of the firing drive train to impart a retraction bias.

* * * * *